US008932731B2

(12) United States Patent
Parham et al.

(10) Patent No.: US 8,932,731 B2
(45) Date of Patent: Jan. 13, 2015

(54) COMPOUNDS FOR ORGANIC ELECTRONIC DEVICES

(75) Inventors: Amir Parham, Frankfurt (DE); Susanne Heun, Bad Soden (DE); Horst Vestweber, Gilserberg (DE); Philipp Stoessel, Frankfurt am Main (DE); Holger Heil, Darmstadt (DE); Rocco Fortte, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 993 days.

(21) Appl. No.: 12/066,554

(22) PCT Filed: Aug. 16, 2006

(86) PCT No.: PCT/EP2006/008053
§ 371 (c)(1),
(2), (4) Date: Aug. 19, 2008

(87) PCT Pub. No.: WO2007/031165
PCT Pub. Date: Mar. 22, 2007

(65) Prior Publication Data
US 2009/0295275 A1    Dec. 3, 2009

(30) Foreign Application Priority Data
Sep. 12, 2005   (DE) .......................... 10 2005 043 163

(51) Int. Cl.
| H01J 1/63 | (2006.01) |
| C07D 221/18 | (2006.01) |
| C09K 11/06 | (2006.01) |
| C07D 471/16 | (2006.01) |
| H01L 51/00 | (2006.01) |
| H05B 33/14 | (2006.01) |
| C09B 17/00 | (2006.01) |
| C09B 19/00 | (2006.01) |
| C09B 21/00 | (2006.01) |
| C09B 23/14 | (2006.01) |
| C09B 57/00 | (2006.01) |
| H01L 51/50 | (2006.01) |

(52) U.S. Cl.
CPC .............. *C09K 11/06* (2013.01); *C07D 471/16* (2013.01); *H01L 51/0059* (2013.01); *H01L 51/0071* (2013.01); *H01L 51/0072* (2013.01); *H05B 33/14* (2013.01); *C09B 17/00* (2013.01); *C09B 19/00* (2013.01); *C09B 21/00* (2013.01); *C09B 23/145* (2013.01); *C09B 23/148* (2013.01); *C09B 57/00* (2013.01); *C09B 57/008* (2013.01); *C09K 2211/1014* (2013.01); *C09K 2211/1029* (2013.01); *H01L 51/0052* (2013.01); *H01L 51/0068* (2013.01); *H01L 51/008* (2013.01); *H01L 51/5012* (2013.01); *H01L 51/5048* (2013.01); *Y02E 10/549* (2013.01); *Y10S 977/754* (2013.01)
USPC ............................. 428/690; 546/38; 977/754

(58) Field of Classification Search
USPC .......................................................... 428/690
See application file for complete search history.

(56) References Cited

U.S. PATENT DOCUMENTS

| 6,875,524 B2 * | 4/2005 | Hatwar et al. ................. 428/690 |
| 2006/0017040 A9 * | 1/2006 | Suzuki et al. ............. 252/301.16 |
| 2006/0149022 A1 | 7/2006 | Parham et al. |

FOREIGN PATENT DOCUMENTS

| DE | 19808088 A1 | 8/1999 | |
| JP | 01076061 | 3/1989 | |
| JP | 05107784 | 4/1993 | |
| JP | 05107784 A * | 4/1993 | ............... G03G 5/06 |
| JP | 07-292362 A | 11/1995 | |
| JP | 08-244127 A | 9/1996 | |
| JP | 11339868 | 12/1999 | |
| JP | 11339868 A * | 12/1999 | ............ H01M 14/00 |
| WO | WO-99/20081 A2 | 4/1999 | |
| WO | WO-2004/070772 A2 | 8/2004 | |

OTHER PUBLICATIONS

Machine English translation of JP 05-107784 A. Oct. 15, 2010.*
Machine English translation of JP 11-339868 A. Oct. 15, 2010.*
Machine English translation of Takizawa (JP 11-339868 A). Sep. 18, 2013.*
Field et al., "Circularly Polarized Luminescence from Bridged Triarylamine Helicenes", *J. A. Chem. Soc.*, vol. 125, pp. 11808-11809 (2003).
Buchanan et al, "Attempts to Prepare Optically Active", *The University, Glasgow*, pp. 2750-2755 (1958).
Bulletin of Faculty of Engineering of Hiroshima University, vol. 4, pp. 275-279 (1955).
Izvestiya Akademii Nauk SSSR, Seriya Khimicheskaya, vol. 1, pp. 150-153 (1978).
Hellwinkel, D., et al., "Zweifach *ortho*-verbrückte Triphenylamin-Derivate", Chem. Ber., 1980, vol. 113, pp. 358-384.
Field, J. E., et al., "Bridged Triarylamines: A New Class of Heterohelicense", J. Org. Chem., 2003, vol. 68, No. 16, pp. 6071-6078.
Kuratsu, M., et al., "2,2':6',2":6",6-Trioxytriphenylamine: Synthesis and Properties of the Radical Cation and Neutral Species", Angew. Chem., 2005, vol. 117, pp. 4124-4126.
Koene, B. E., et al., "Asymmetric Triaryldiamines as Thermally Stable Hole Transporting Layers for Organic Light-Emitting Devices", Chem. Mater., 1998, vol. 10, pp. 2235-2250.

(Continued)

*Primary Examiner* — J. L. Yang
(74) *Attorney, Agent, or Firm* — Drinker Biddle & Reath LLP

(57) ABSTRACT

The present invention relates to the improvement of organic electroluminescent devices, in particular blue-emitting devices, by using compounds of the formula (1) or formula (2) as dopants in the emitting layer or as hole-transport material in a hole-transport layer.

22 Claims, No Drawings

(56) References Cited

OTHER PUBLICATIONS

Field, J. E., et al., "Heterotriangulenes—Structure and Properties", Chem. Mater., 2002, vol. 14, pp. 962-964.
Kuratsu, M., et al., "Synthesis, Structure, and Electron-Donating Ability of 2,2':6',2"- Dioxatriphenylamine", Chemistry Letters, 2004, vol. 33, No. 9, pp. 1174-1175.
Field, J. E., et al., "Spontaneous assembly of a hydrogen-bonded tetrahedron", Chem. Comm., 2002, pp. 2260-2261.
Hellwinkel, D., et al., "Zur Stereochemie verbrückter Triarylamine", Chem. Ber., 1974, vol. 107, pp. 616-626.
Hellwinkel, D., et al., "12-Organyldibenz(b,g)azocin-5,7-dione", Chem. Ber., 1986, vol. 119, pp. 3165-3197.

* cited by examiner

COMPOUNDS FOR ORGANIC ELECTRONIC DEVICES

RELATED APPLICATIONS

This application is a national stage application (under 35 U.S.C. § 371) of PCT/EP2006/008053 filed, Aug. 16, 2006, which claims benefit of German application 10 2005 043 163.1, filed Sep. 12, 2005.

The present invention describes novel compounds and the use thereof in organic electroluminescent devices.

Organic semiconductors are being developed for a number of different applications which can be ascribed to the electronics industry in the broadest sense. The construction of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, these devices still exhibit considerable problems which require urgent improvement:

1. The efficiency is still too low, in particular in the case of fluorescent OLEDs, and has to be improved.
2. The operating lifetime is still inadequate, in particular in the case of blue emission, meaning that it has hitherto only been possible to achieve simple applications commercially.
3. The operating voltage is quite high, especially in the case of fluorescent OLEDs, and should therefore be reduced further in order to improve the power efficiency. This is of major importance, in particular, for mobile applications.
4. Many blue-emitting emitters which comprise aromatic amines are thermally unstable and decompose on sublimation or on vapour deposition. The use of these systems is thus impossible or is only possible with major losses and with high technical complexity.

Owing to their physical, photochemical and electrochemical properties, materials based on arylamines have been investigated in detail as hole-transport or emitter materials; they form uniform amorphous layers and can form stable free-radical cations without changing chemically.

Organic compounds which have proven successful as hole conductors are generally derived from diarylamino-substituted triphenylamine (TPA type), from diarylamino-substituted biphenyl (TPD type) or combinations of these basic compounds (TPTE types). Furthermore, tristilbenamines (for example TSA and MSA) containing phenylene-vinylene structural elements have also proven to be suitable materials which ensure efficient hole conduction.

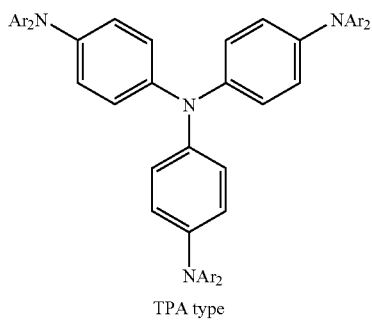

TPA type

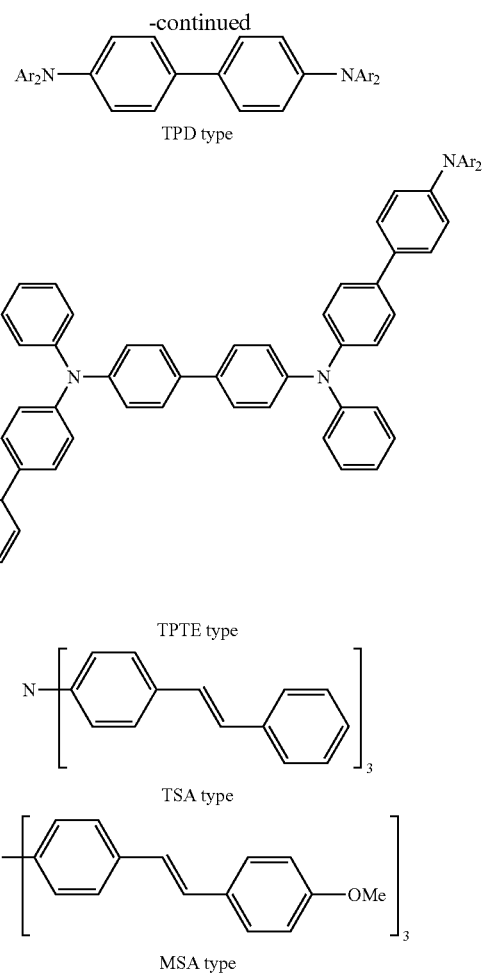

Surprisingly, it has now been found that a novel class of triarylamines has further improved electronic properties. These compounds contain a rigid planar triphenylamine unit and flexible structural elements in the outer periphery, reducing the flexibility of the molecule centre and increasing the solubility due to substituents; in addition, compounds which can be employed as emitters can be synthesised by extending the π-electron system in the outer periphery. In addition, planar, stable triarylamine free-radical cations can be used as electronic and magnetic materials.

A number of di- and tri-ortho-bridged triphenylamines have already been synthesised in the 1970s, but have not been investigated in detail with respect to their physical properties (D. Heliwinkel, M. Melan, Chem. Ber. 1974, 107, 616-626; D. Hellwinkel, W. Schmidt, Chem. Ber. 1980, 113, 358-384). A further development in this respect is the synthesis of the unsubstituted triphenylamine skeleton which is bridged via keto groups in the ortho-position (J. E. Field, T. J. Hill, D. Venkataraman, J. Org. Chem. 2003, 68, 6071-6078; J. E. Field, D. Venkataraman, Chem. Mater. 2002, 14, 962-964), and the synthesis of the unsubstituted triphenylamine skeleton which is bridged via ether groups in the ortho-position. These compounds form stable free-radical cations (M. Kuratsu, M. Kozaki, K. Okada, Angew. Chem. 2005, 117, 4124-4126). However, a disadvantage of these compounds, in particular those which are linked via keto groups, is their very low solubility in common organic solvents, which hinders or prevents efficient purification by recrystallisation or chromatography. This applies, in particular, to the purification of relatively large amounts, as are required in display manufacture.

Surprisingly, it has been found that the compounds according to the invention have excellent properties as emitters and hole conductors in OLEDs.

The compounds according to the invention absorb and emit at longer wavelengths than the analogous unbridged representatives. Significantly more intense emission is observed in the case of bridging of the phenylamine unit. Furthermore, these compounds have higher hole mobility.

The compounds according to the invention can be prepared reproducibly in high purity and have no batch variation. An industrial process for the production of the electroluminescent devices according to the invention is therefore significantly more efficient.

The compounds according to the invention are distinguished by good solubility in organic solvents, which considerably simplifies purification and processing thereof. These compounds can thus also be processed from solution by coating or printing techniques. This property is also advantageous in the case of conventional processing by evaporation, since cleaning of the equipment and the shadow masks employed is thus considerably simplified. The compounds according to the invention are furthermore distinguished by improved oxidation stability in solution, which on the one hand has a positive effect on purification and on the other hand generally on handling of these compounds since the storage stability of solutions prepared for processing by printing processes is significantly improved. The compounds according to the invention are in addition distinguished by high temperature stability, enabling them to be evaporated in a high vacuum without decomposition. This property is a fundamental prerequisite for the reproducible production of OLED devices and has, in particular, a positive effect on the operating lifetime.

The present invention therefore relates to these compounds and to the use thereof in OLEDs.

The invention relates to compounds of the formula (1) and formula (2)

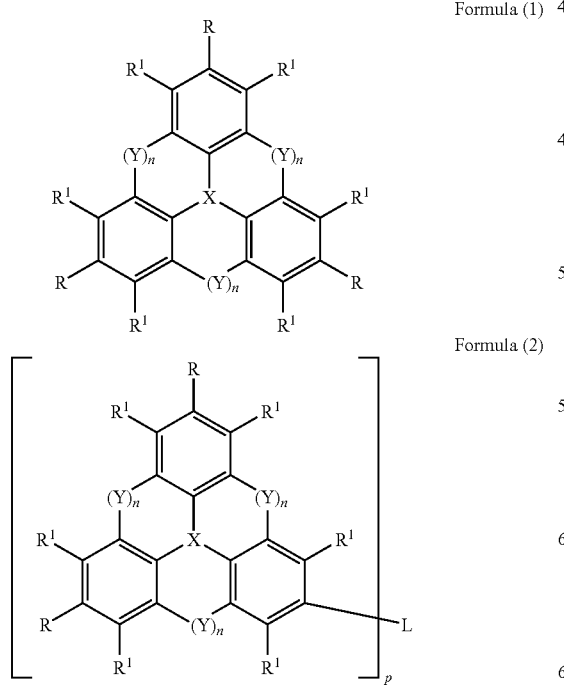

where the following applies to the symbols and indices used:

X is on each occurrence, identically or differently, N, P, As, Sb, P=O, As=O or Sb=O, Y is, identically or differently on each occurrence, O, S, $C(R^1)_2$, C=O, C=S, C=NR$^1$, C=C(R$^1$)$_2$, Si(R$^1$)$_2$, BR$^1$, NR$^1$, PR$^1$, AsR$^1$, SbR$^1$, BiR$^1$, P(=O)R$^1$, As(=O)R$^1$, Bi(=O)R$^1$, SO, SeO, TeO, SO$_2$, SeO$_2$, TeO$_2$ or a chemical bond;

R$^1$ is on each occurrence, identically or differently, H, OH, F, Cl, Br, I, CN, CHO, NO$_2$, N(Ar)$_2$, Si(R$^2$)$_3$, B(OR$^2$)$_2$, C(=O)Ar, P(=O)Ar$_2$, S(=O)Ar, S(=O)Ar$_2$, CR$^2$=CR$^2$Ar, C=CAr, OSO$_2$R$^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals R$^2$, where one or more non-adjacent CH$_2$ groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, P(=O)R$^2$, S=O, SO$_2$, NR$^2$, —O—, —S— or —CONR$^2$— and where one or more H atoms may be replaced by F, Cl, Br, I, CN or NO$_2$, or an aromatic or heteroaromatic ring system having 5 to 40 aromatic ring atoms, which may be substituted by one or more radicals R$^2$, or an aryloxy or heteroaryloxy group having 5 to 24 aromatic ring atoms, which may be substituted by one or more radicals R$^2$, or a combination of two, three, four or five of these systems; two or more substituents R$^1$ here, both on the same ring and also on different rings, may also form a mono- or polycyclic, aliphatic, aromatic or heteroaromatic ring system with one another;

R is defined like R$^1$, where at least one radical R is not equal to hydrogen;

R$^2$ is on each occurrence, identically or differently, H or an aliphatic, aromatic and/or heteroaromatic hydrocarbon radical having 1 to 20 C atoms, where two or more radicals R$^2$ may also form a ring system with one another;

Ar is on each occurrence, identically or differently, an aromatic or heteroaromatic ring system having 5-30 aromatic ring atoms, which may be substituted by one or more non-aromatic radicals R$^1$;

L is an at least divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, each of which may be substituted by one or more radicals R$^2$, where one or more non-adjacent CH$_2$ groups may be replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, P(=O) R$^2$, S=O, SO$_2$, —O—, —S— or —CONR$^2$— and where one or more H atoms may be replaced by F, Cl, Br, I, CN or NO$_2$, or an at least divalent aromatic or heteroaromatic ring system having 5 to 40 aromatic ring atoms, which may be substituted by one or more radicals R$^2$, or P(R$^1$)$_{3-p}$, P(=O) (R$^1$)$_{3-p}$, C(R$^1$)$_{4-p}$, Si(R$^1$)$_{4-p}$, N(Ar)$_{3-p}$ or a combination of two, three, four or five of these systems; or L is a chemical bond;

n is on each occurrence, identically or differently, 0, 1 or 2, where n=0 means that a hydrogen or radical R$^1$ is present instead of Y, with the proviso that at least two indices n are not equal to 0;

p is 2, 3, 4, 5 or 6, with the proviso that p is not greater than the maximum valency of L;

the following compound is excluded from the invention:

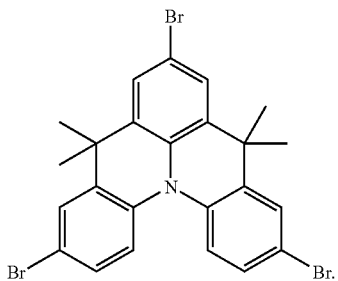 [SMILES: CC1(C)c2cc(Br)ccc2N2c3ccc(Br)cc3C(C)(C)c3cc(Br)cc1c32]

Although this is evident from the above description, it should be explicitly emphasised here that one or more radicals R in formula (1) or formula (2) may also in turn stand for a bridged triarylamine system of the formula (1) or formula (2). It is thus also possible for two or three part-structures of the formula (1) or formula (2) to be linked to one another in a linear manner or for four part-structures of the formula (1) to be linked to one another in a star-shaped manner and to form a dendritic system.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the total number of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an sp$^3$-hybridised C, N or O atom. Thus, for example, systems such as 9,9'-spirobifluorene, 9,9-diarylfluorene, triarylamine, diaryl ether, etc., are also intended to be taken to mean aromatic ring systems for the purposes of this invention.

For the purposes of this invention, an aryl group or heteroaryl group is taken to mean an aromatic group or heteroaromatic group having a common aromatic electron system. For the purposes of this invention, this can be a simple homo- or heterocycle, for example benzene, pyridine, thiophene, etc., or it can be a condensed aromatic ring system in which at least two aromatic or heteroaromatic rings, for example benzene rings, are "fused" to one another, i.e. are condensed onto one another by anellation, i.e. have at least one common edge and thus also a common aromatic system. These aryl or heteroaryl groups may be substituted or unsubstituted; any substituents present may likewise form further ring systems. Thus, for example, systems such as naphthalene, anthracene, phenanthrene, pyrene, etc. should be regarded as aryl groups and quinoline, acridine, benzothiophene, carbazole, etc., as heteroaryl groups for the purposes of this invention, while, for example, biphenyl, fluorene, spirobifluorene, etc., do not represent aryl groups since they involve separate aromatic electron systems.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-40 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formula (1) and formula (2) in which the symbol X stands for nitrogen, phosphorus or P=O, particularly preferably for nitrogen or phosphorus, very particularly preferably for nitrogen.

Preference is furthermore given to compounds of the formula (1) and formula (2) in which the symbols Y, identically or differently on each occurrence, stand for O, S, $(CR^1)_2$, C=O, P(=O)R$^1$, C=C(R$^1$)$_2$, NR$^1$, SO or SO$_2$ or a chemical bond, particularly preferably for O, S, C=O or C(R$^1$)$_2$ which is substituted by two identical radicals R$^1$, very particularly preferably for O, C=O or C(R$^1$)$_2$ which is substituted by two identical radicals R$^1$, preferably alkyl substituents, in particular methyl substituents, in particular for C(R$^1$)$_2$ which is substituted by two identical radicals R$^1$, preferably methyl substituents.

Preference is given to compounds of the formula (1) and formula (2) in which the symbol R$^1$, identically or differently on each occurrence, stands for H, F, CF$_3$, OCH$_3$, OCF$_3$ or an aliphatic, aromatic or heteroaromatic hydrocarbon radical having up to 10 C atoms, particularly preferably for H, F or an aliphatic or aromatic hydrocarbon radical having up to 6 C atoms, very particularly preferably for H or an aliphatic hydrocarbon having 1 to 4 C atoms. R$^1$ on the bridges Y particularly preferably stands for an aliphatic hydrocarbon radical having 1 to 6 C atoms, very particularly preferably for methyl, or for an aryl or heteroaryl group having 6 to 10 C atoms, very particularly preferably for phenyl; furthermore, two radicals R$^1$ on the same bridge Y may form a ring system with one another and thus build up a spiro system.

In a preferred embodiment of the invention, at least two radicals R are not equal to hydrogen; in a particularly preferred embodiment of the invention, all three radicals R are not equal to hydrogen.

Preference is furthermore given to compounds of the formula (1) and formula (2) in which the symbol R on each occurrence, identically or differently, stands for F, Cl, Br, I, CHO, $B(OR^2)_2$, $P(R^2)_2$, $N(Ar)_2$, $CR^2{=}CR^2Ar$, $C{\equiv}CAr$ or an aromatic or heteroaromatic ring system having 5 to 30 aromatic ring atoms, which may be substituted by one or more non-aromatic radicals $R^1$, or a combination of two, three, four or five of these radicals. R is particularly preferably on each occurrence, identically or differently, F, Br, $B(OR^2)_2$, $N(Ar)_2$, $CR^2{=}CR^2Ar$ or an aromatic or heteroaromatic ring system having 5 to 25 aromatic ring atoms, which may in each case be substituted by one or more non-aromatic radicals $R^1$, or a combination of two, three or four of these radicals. R is very particularly preferably on each occurrence, identically or differently, $N(Ar)_2$, $CR^2{=}CR^2Ar$ or an aromatic or heteroaromatic ring system having 6 to 20 aromatic ring atoms, which may be substituted by one or more non-aromatic radicals $R^2$, or a combination of two or three of these radicals.

Preference is furthermore given to compounds of the formula (1) and formula (2) in which the symbol Ar, identically or differently on each occurrence, stands for an aromatic ring system having 6 to 25 aromatic ring atoms, in particular benzene, naphthalene or spirobifluorene, which may in each case be substituted by one or more radicals $R^1$. Very particular preference is given to phenyl, ortho-, meta- or para-tolyl, para-fluorophenyl, 1-naphthyl and 2-naphthyl.

Preference is furthermore given to compounds of the formula (2) in which the symbol L stands for $-CR^2{=}CR^2-$, $-C{\equiv}C-$, $C{=}O$, $S{=}O$, $SO_2$, $-O-$, $-S-$, $P(R^1)_{3-p}$, $P({=}O)(R^1)_{3-p}$, $C(R^1)_{4-p}$, $Si(R^1)_{4-p}$, $N(Ar)_{3-p}$ or an aromatic or heteroaromatic ring system having 6 to 30 aromatic ring atoms, which may be substituted by one or more radicals $R^2$ or a combination of two, three or four of these systems or a chemical bond. The symbol L particularly preferably stands for $-CR^2{=}CR^2-$, $C{=}O$, $-O-$, $P(R^1)_{3-p}$, $P({=}O)(R^1)_{3-p}$, $C(R^1)_{4-p}$, $N(Ar)_{3-p}$ or an aromatic or heteroaromatic ring system having 6 to 25 aromatic ring atoms, which may be substituted by one or more radicals $R^2$, or a combination of two or three of these systems or a chemical bond. The symbol L very particularly preferably stands for $-CR^2{=}CR^2-$, $C{=}O$, $P({=}O)(R^1)_{3-p}$, $N(Ar)_{3-p}$ or an aromatic or heteroaromatic ring system having 6 to 14 aromatic ring atoms or spirobifluorene, each of which may be substituted by one or more radicals $R^2$, or a chemical bond.

Preference is furthermore given to compounds in which the index n, identically or differently on each occurrence, stands for 0 or 1, where n=0 means that hydrogen or a radical $R^1$ is present instead of Y, with the proviso that at least two indices n are not equal to 0; the index n is particularly preferably=1.

Preference is furthermore given to compounds of the formula (2) in which the index p is equal to 2, 3, 4 or 5, particularly preferably 2, 3 or 4, very particularly preferably 2 or 3, with the proviso that p is not greater than the maximum valency of L.

If the compound is able to form enantiomers or diastereomers, the invention in each case relates both to mixtures of the diastereomers or enantiomers and also to the enriched or isolated diastereomers or enantiomers. If the compound is able to exhibit atropisomerism about one or more bonds, the invention in each case also relates to the isolated or enriched atropisomers. This relates both to enantiomers and also to diastereomers.

Examples of preferred compounds of the formula (1) are structures (1) to (48) depicted below.

Structure (1)

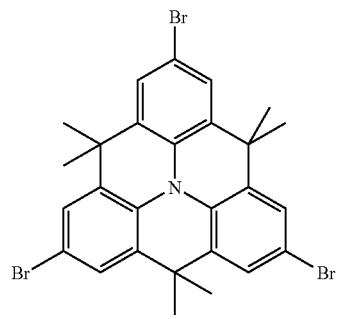

Structure (2)

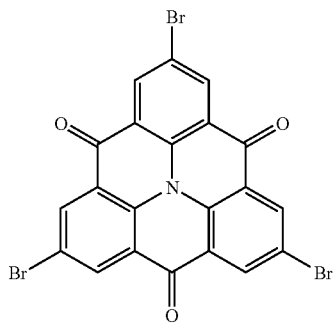

Structure (3)

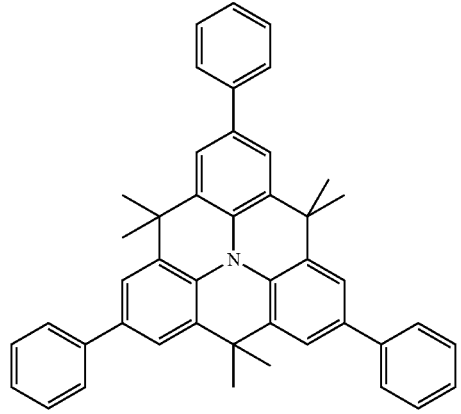

Structure (4)

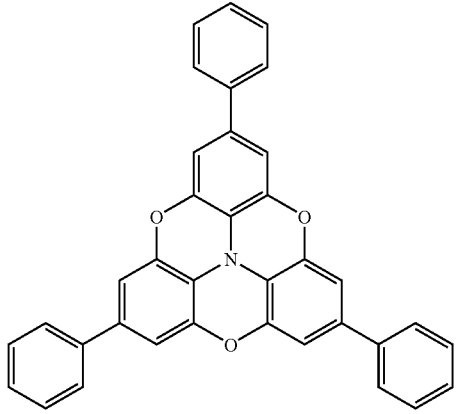

-continued
Structure (5)
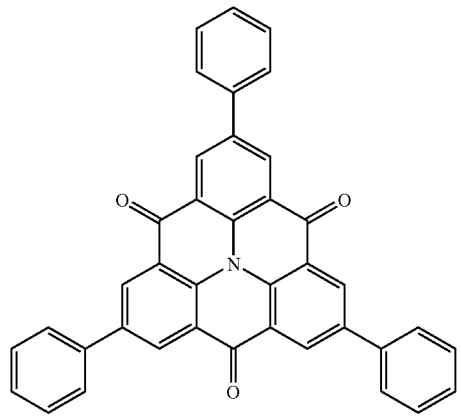
Structure (6)
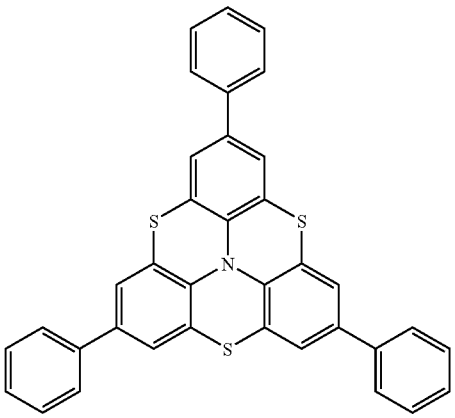
Structure (7)
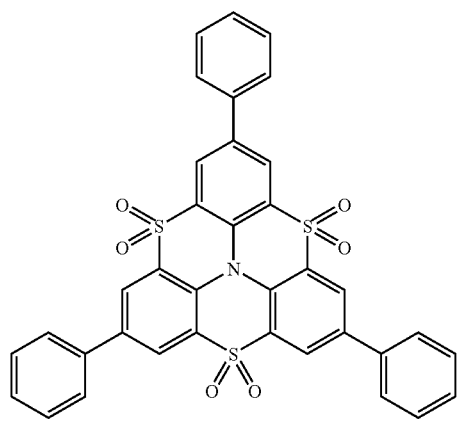
Structure (8)
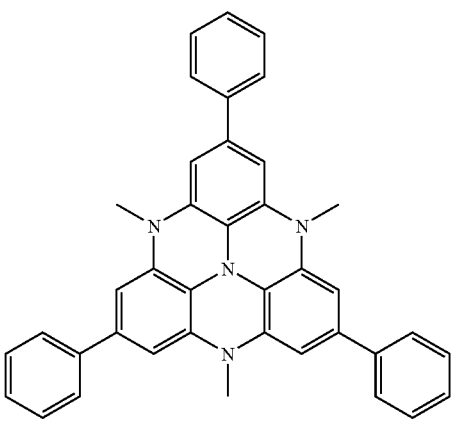
Structure (9)
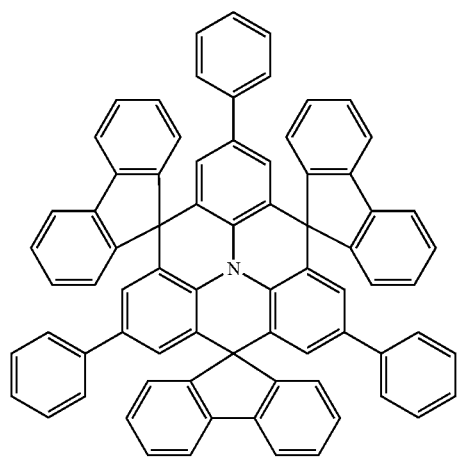
Structure (10)
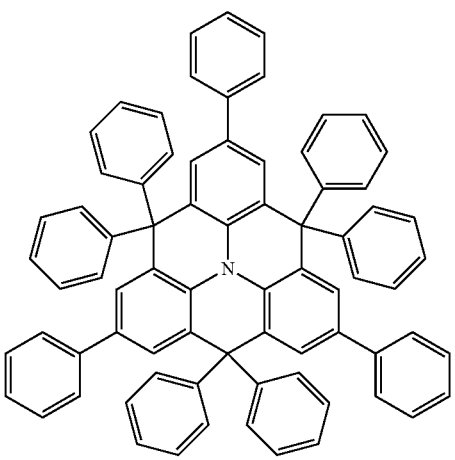

-continued
Structure (11)
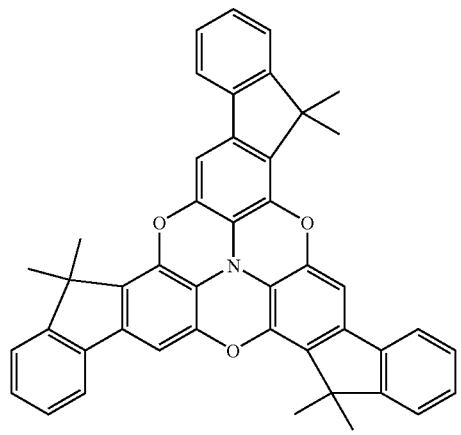
Structure (12)
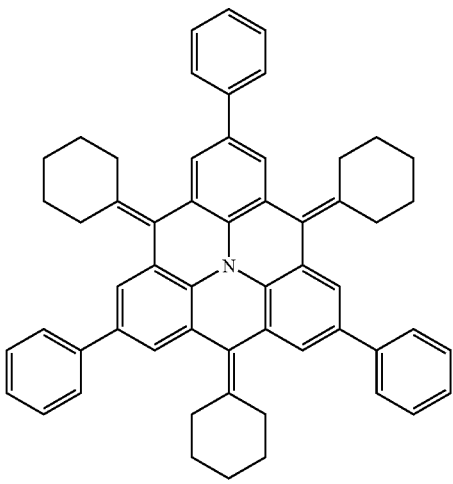
Structure (13)
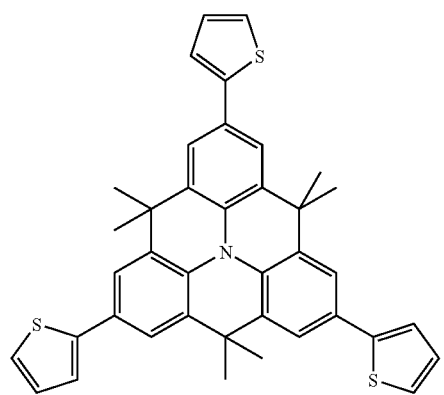
Structure (14)
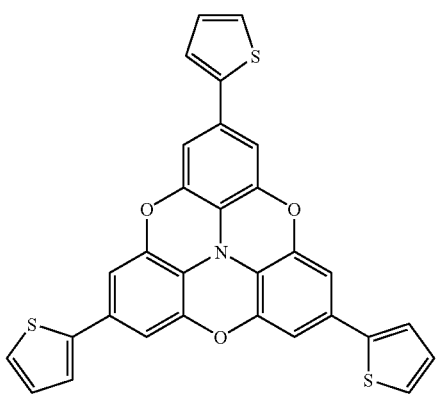
Structure (15)
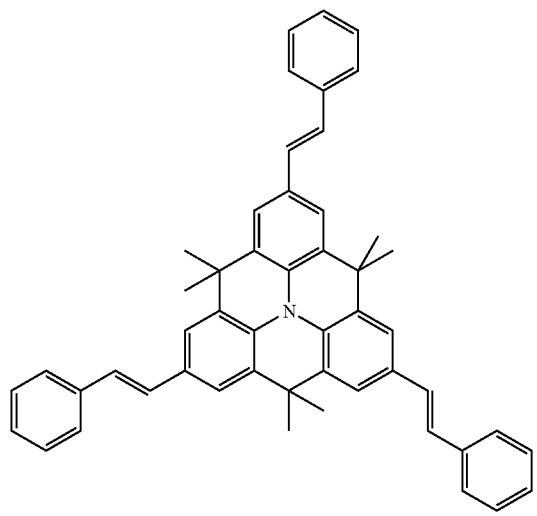
Structure (16)
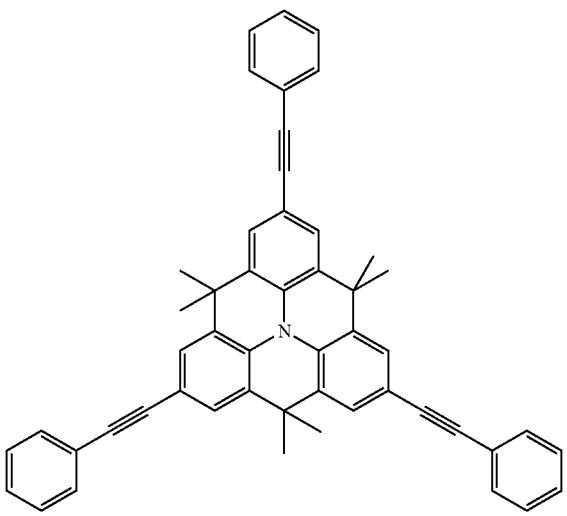

-continued
Structure (17)
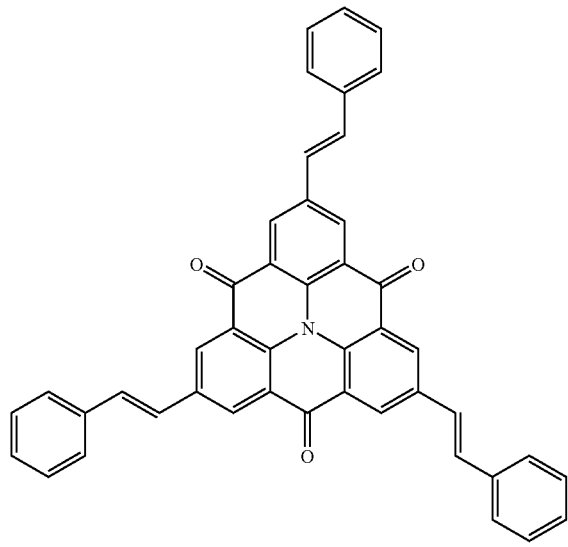
Structure (18)
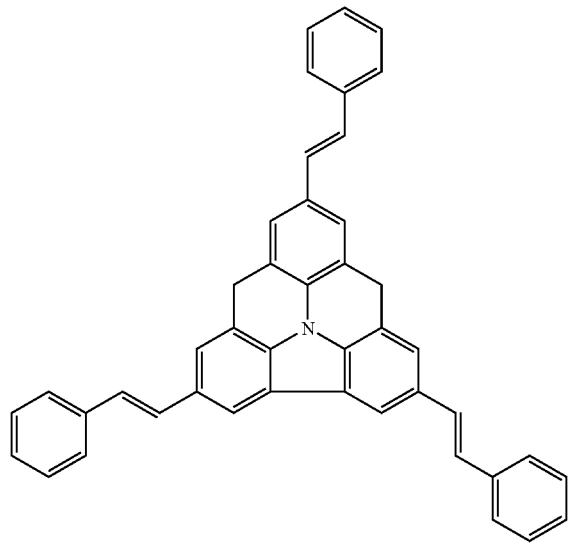
Structure (19)
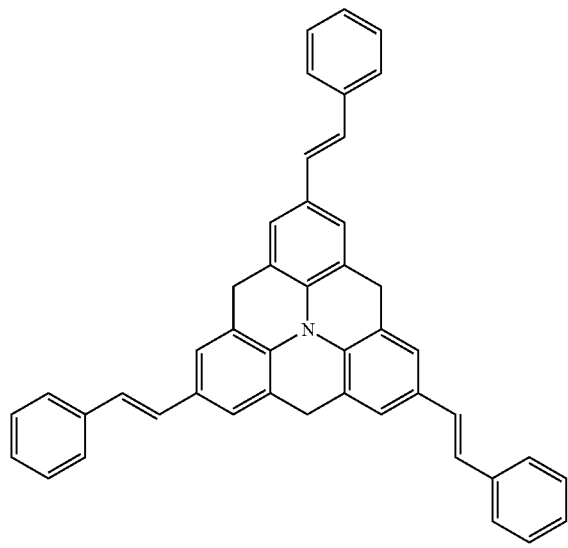
Structure (20)
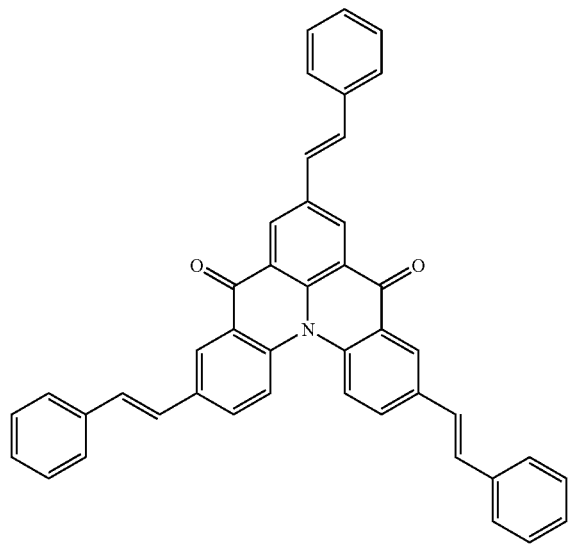

-continued
Structure (21)
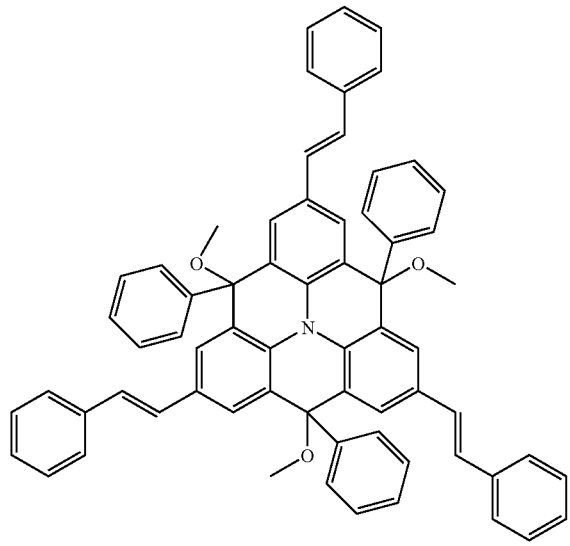
Structure (22)
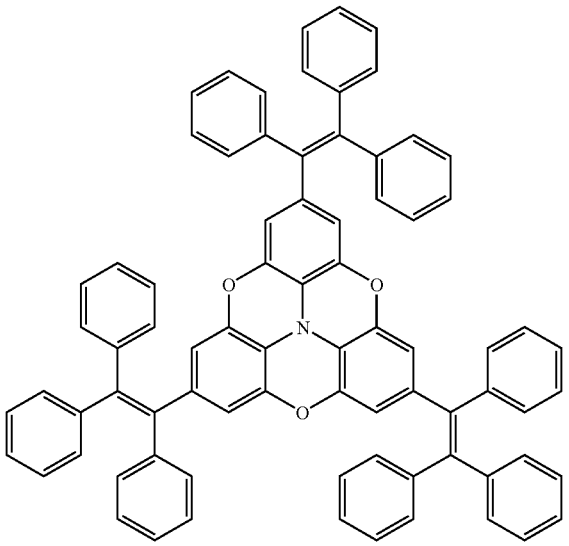
Structure (23)
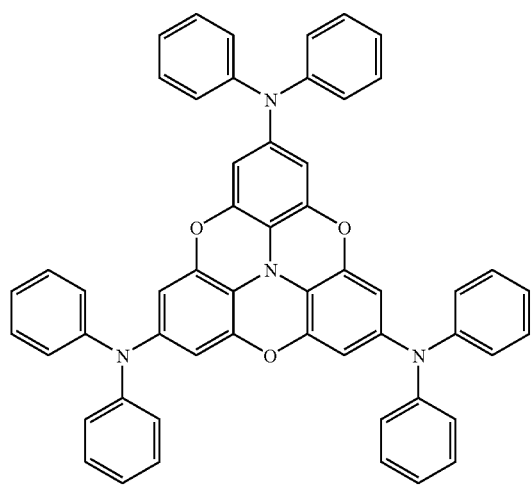
Structure (24)
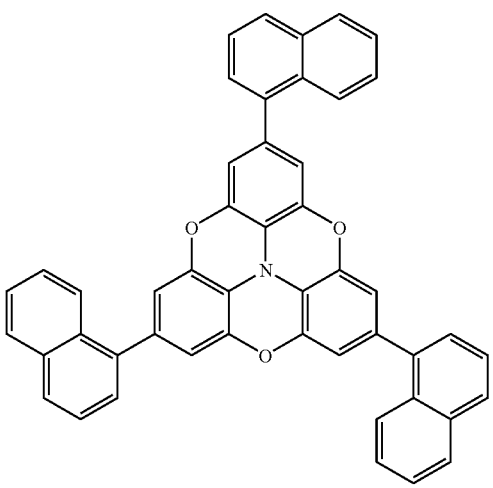
Structure (25)
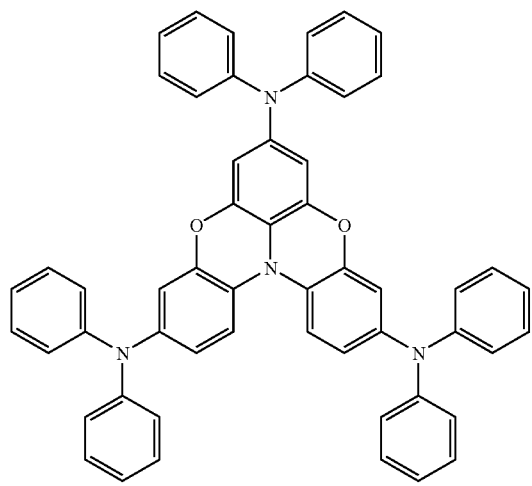
Structure (26)
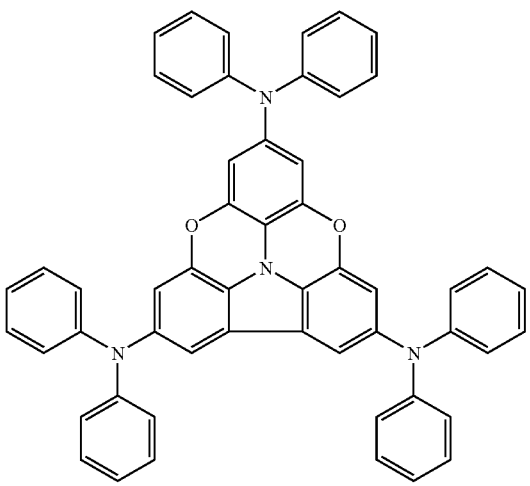

Structure (27)
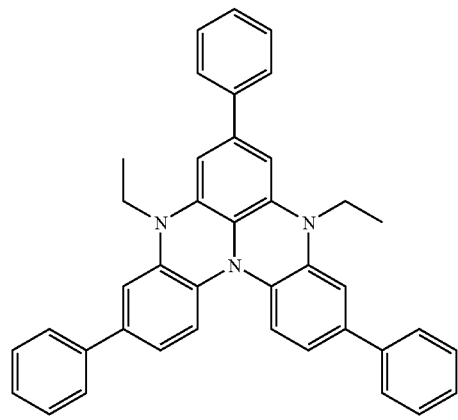
Structure (28)
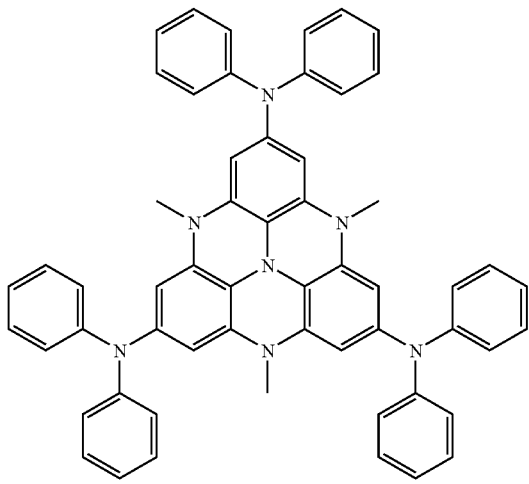
Structure (29)
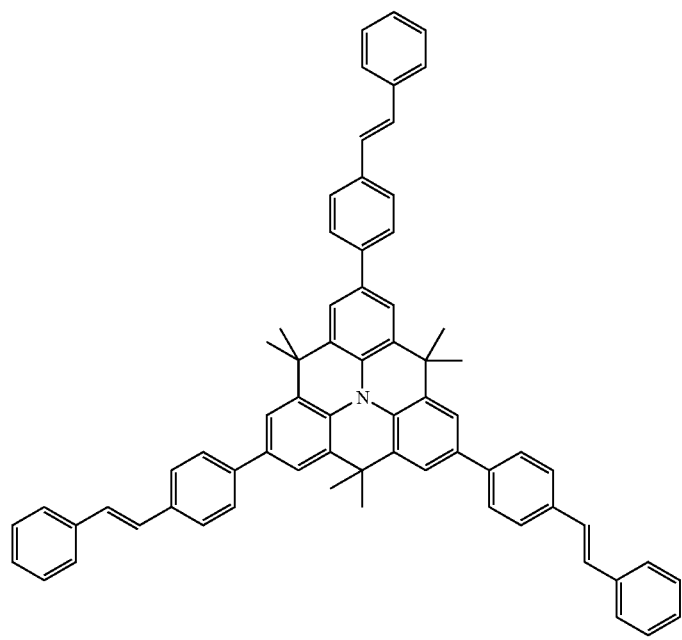

Structure (30)
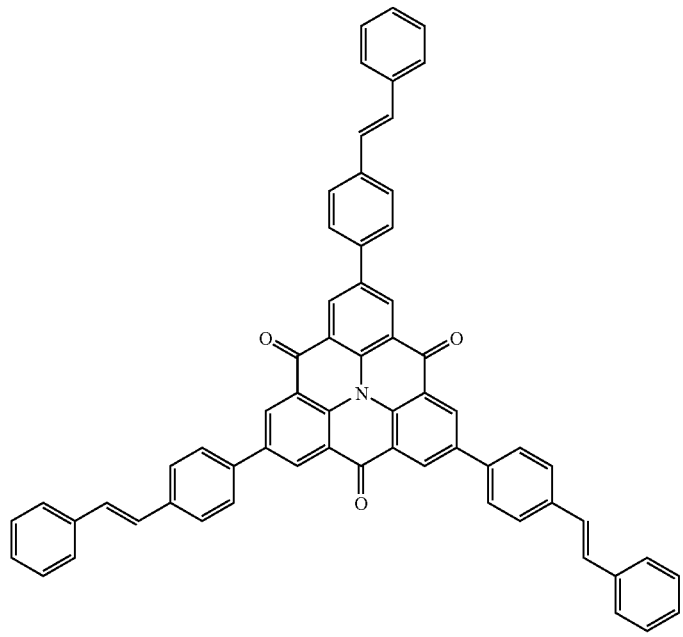
Structure (31)
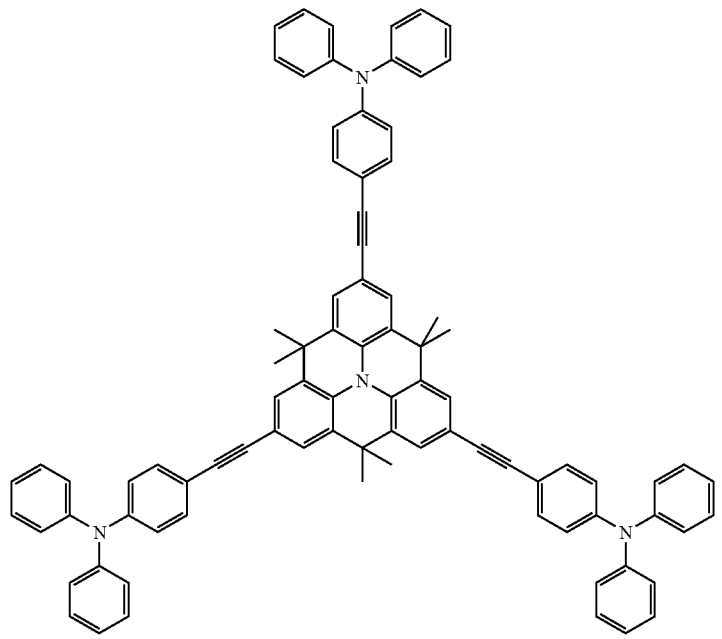

Structure (32)
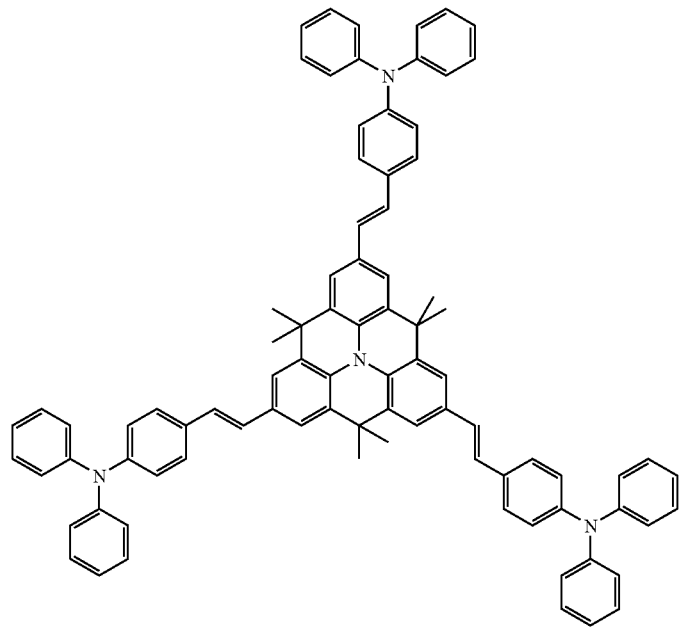
Structure (33)
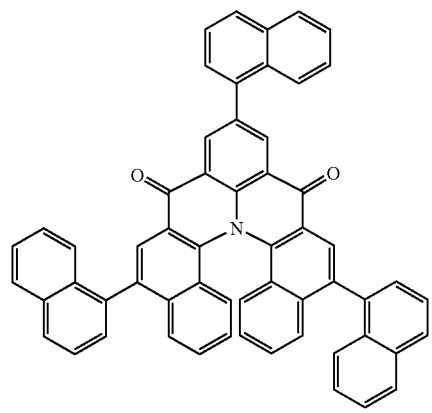
Structure (34)
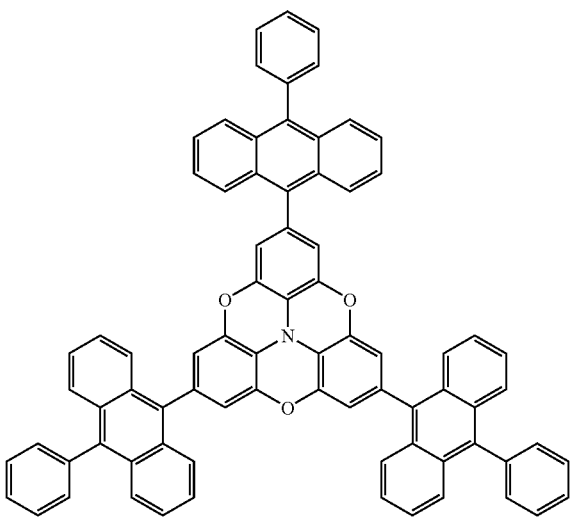

-continued
Structure (35)
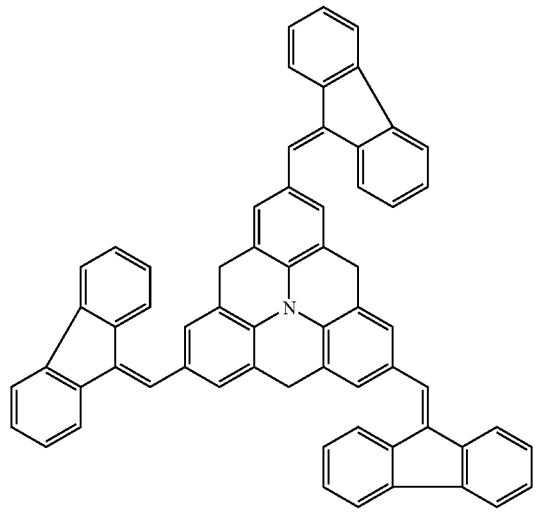
Structure (36)
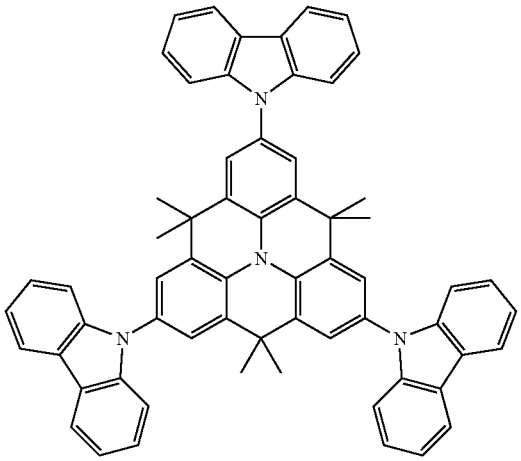
Structure (37)
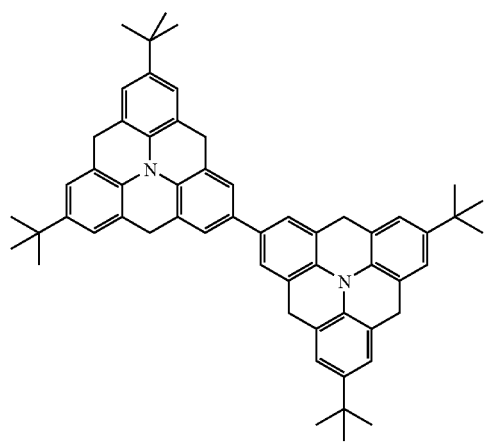
Structure (38)
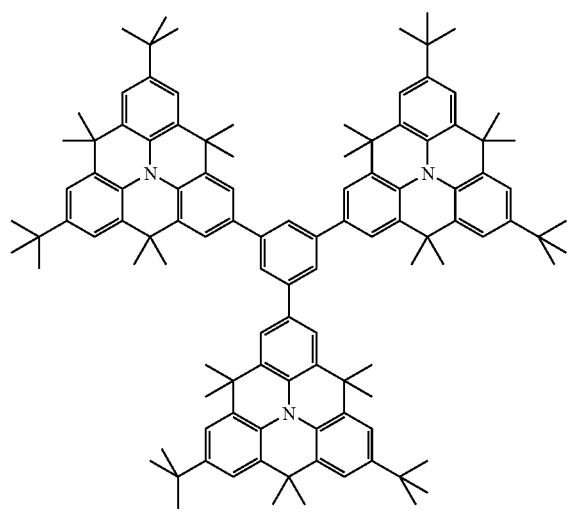
Structure (39)
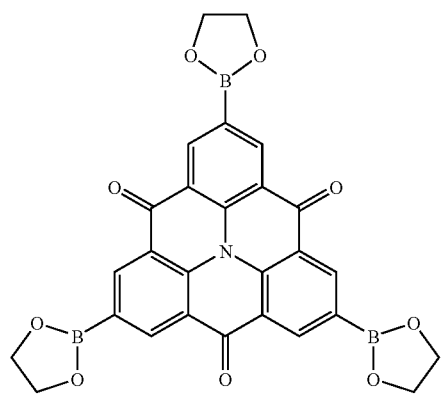
Structure (40)
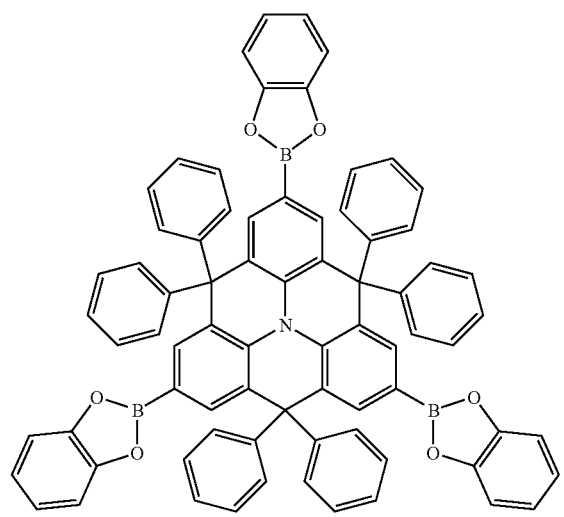

-continued
Structure (41)
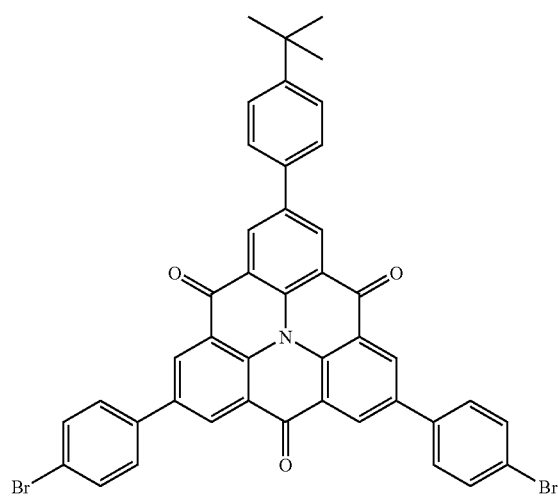
Structure (42)
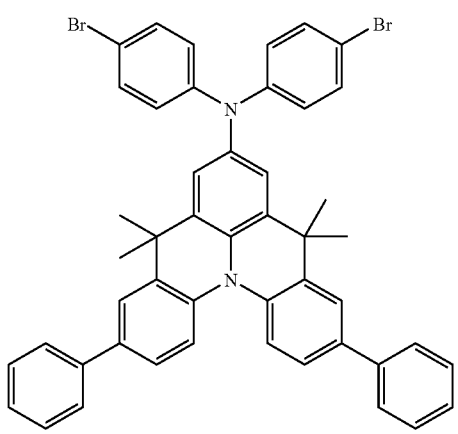
Structure (43)
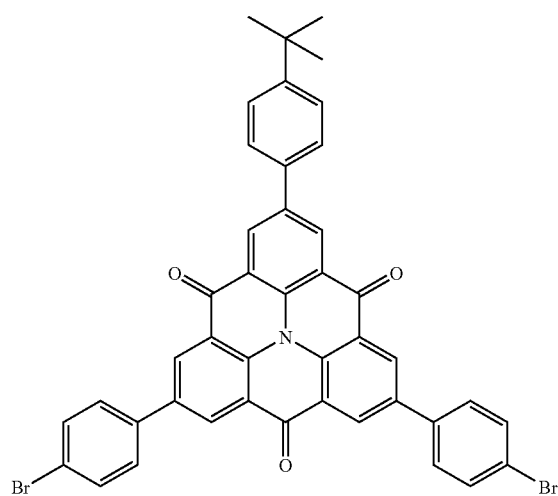
Structure (44)
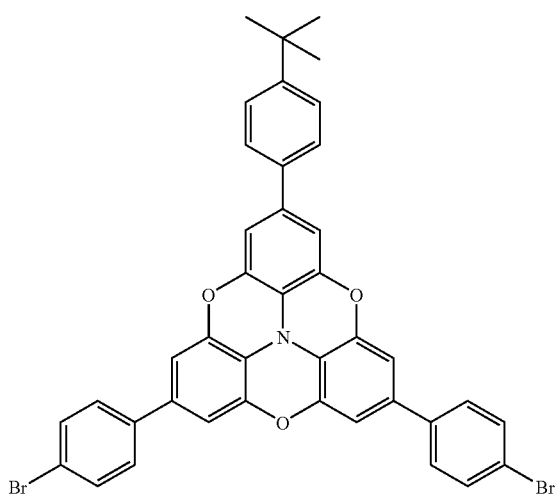
Structure (45)
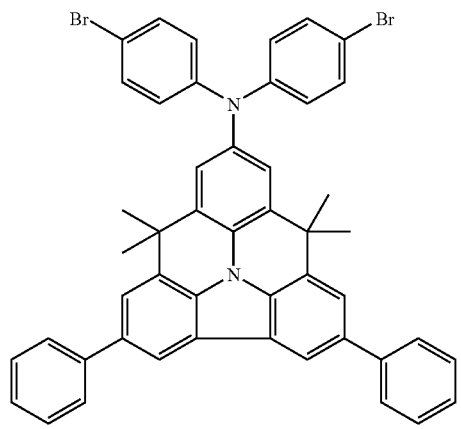
Structure (46)
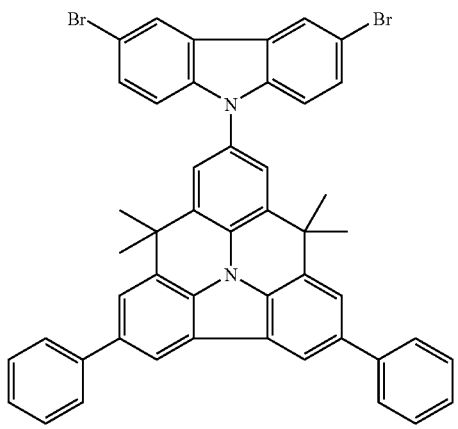

Structure (47)

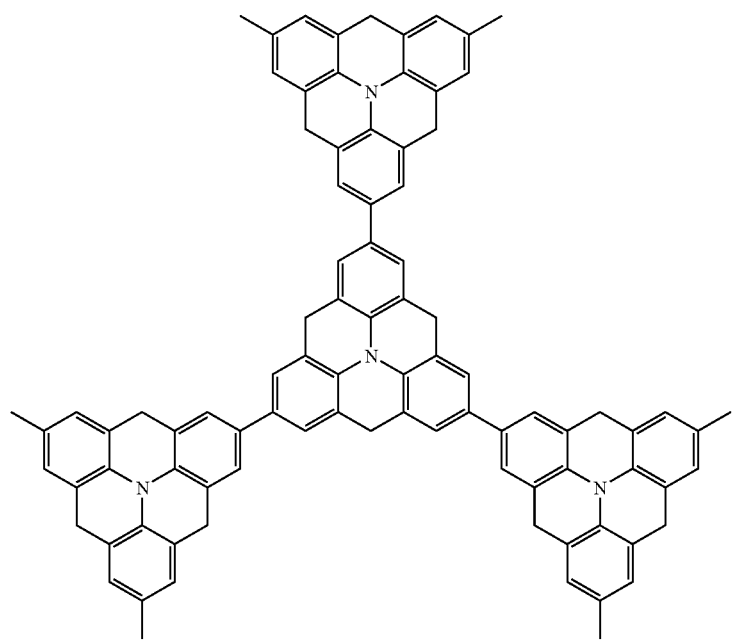

Structure (48)

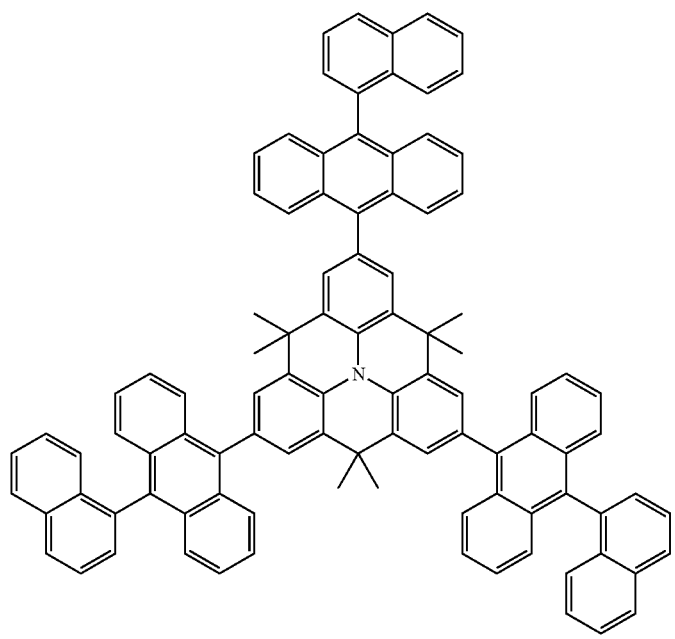

The physical properties can be influenced and optimised through a specific choice of the bridging unit Y. The determining structural element of this novel class of compounds is the planar triphenylamine unit with its low ionisation potential, while the substituents and the choice of the bridge Y are crucial for the emission and for the physical parameters in the solid state (melting point, glass transition point, amorphous behaviour).

The interaction of the units, depending on the choice of substituents, can be influenced by the derivatisation and extension of the π-system in the planar triphenylamine system, and an increase in solubility can thus be facilitated.

The ability to form columnar π-stacks due to the planarity of the central units furthermore also makes this class of molecules an ideal conjugated, electro-active building block for three-dimensional networks and discotic liquid crystals.

Preferred embodiments of the compounds according to the invention are those in which the glass transition temperature $T_g$ is greater than 90° C., preferably greater than 100° C., particularly preferably greater than 120° C.

The skeletons of the compounds according to the invention can be prepared by synthetic steps known to the person skilled in the art, such as, for example, bromination, Ullmann arylation, Hartwig-Buchwald coupling, etc., as depicted in scheme 1 and scheme 2.

These skeletons can be functionalised in a further step. Thus, the bromination of triphenylamines containing bridge elements results in tri-p-bromine-substituted bridged triphenylamines, where, due to the +M-directing effect of the nitrogen atom, good yields are achieved here at the same time as excellent regioselectivities. Brominating agents which can be used besides elemental bromine are, in particular, also N-bromo compounds, such as N-bromosuccinimide (NBS). Functionalisation using other reactive groups, for example chlorine, iodine, boronic acid or boronic acid derivatives, triflate or tosylate, is likewise suitable.

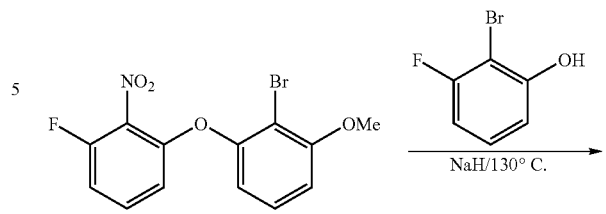

Scheme 1: Synthesis of the skeleton

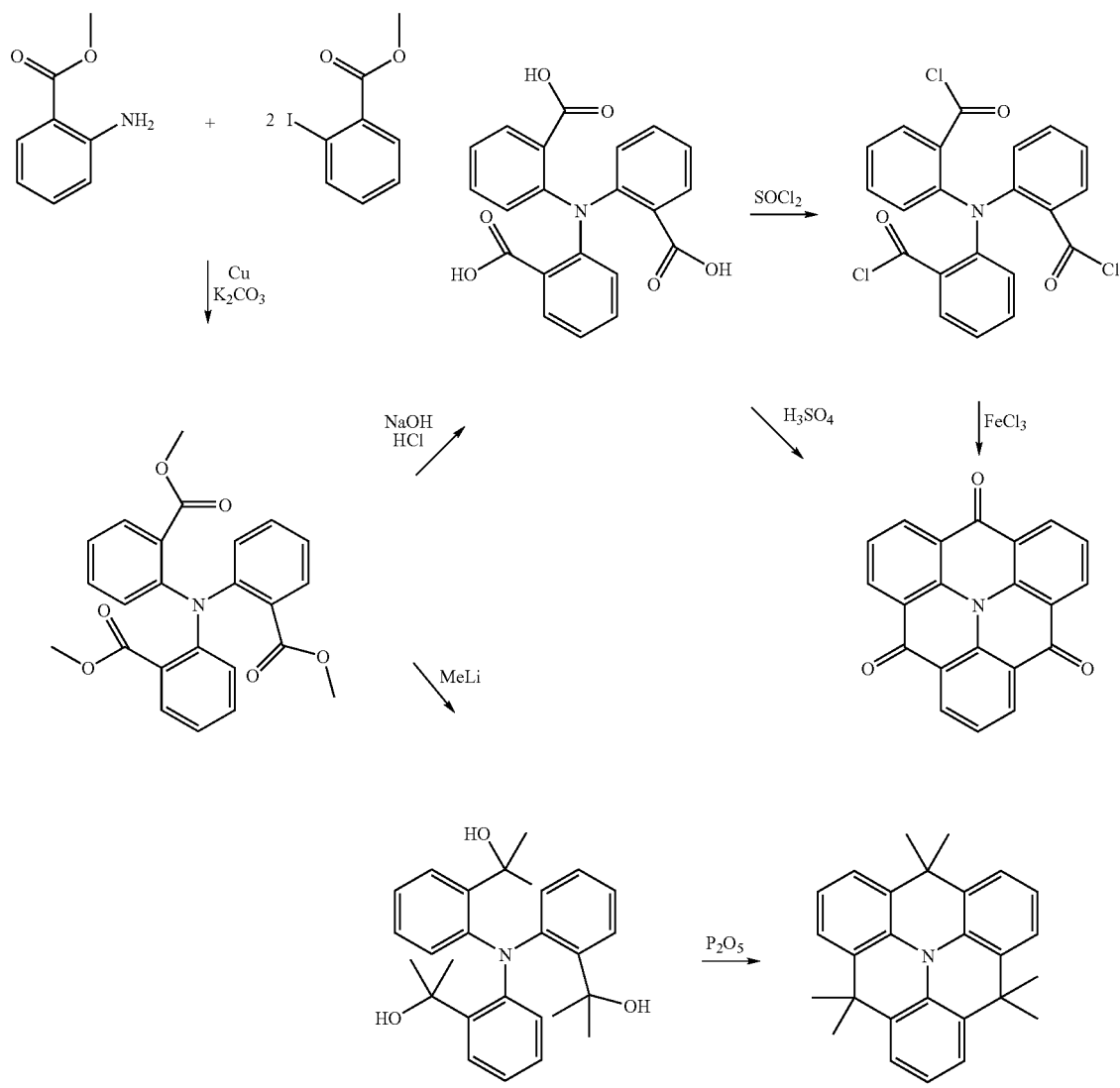

Scheme 2: Synthesis of the skeleton

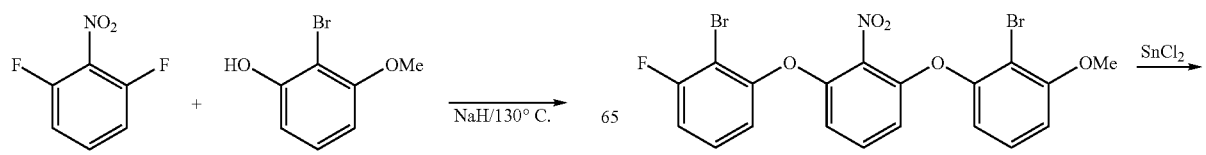

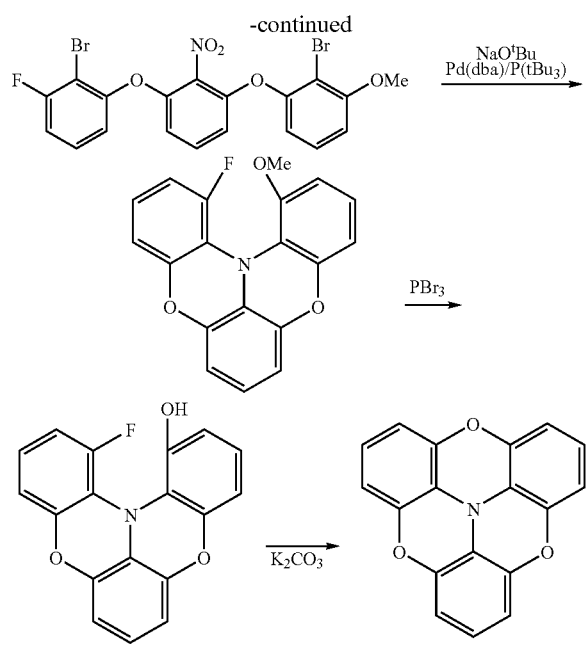

Scheme 3: Functionalisation of the skeleton

The functionalised, in particular brominated compounds represent the central unit for the further functionalisation, as depicted in scheme 3. Thus, these functionalised, bridged compounds can be converted into compounds of the formula (1), for example by Suzuki coupling to functionalised arylboronic acids. Other coupling reactions (for example Stille coupling, Heck coupling, Sonogashira coupling, etc.) can likewise be used. Coupling to diarylamines by the Hartwig-Buchwald method results in triarylamine derivatives. Correspondingly, aliphatic amines, carbazoles, etc., can be introduced as substituents. Furthermore, formyl, alkylcarbonyl and arylcarbonyl groups or protected analogues thereof, for example in the form of the corresponding dioxolanes, are suitable as functionalisation. The resultant carbonyl substrates can easily be converted into the corresponding olefins, for example by a Wittig-Horner reaction. The brominated compounds can furthermore be lithiated and converted into ketones by reaction with electrophiles, such as benzonitrile, and subsequent acidic hydrolysis or into phosphine oxides using chlorodiphenylphosphines and subsequent oxidation.

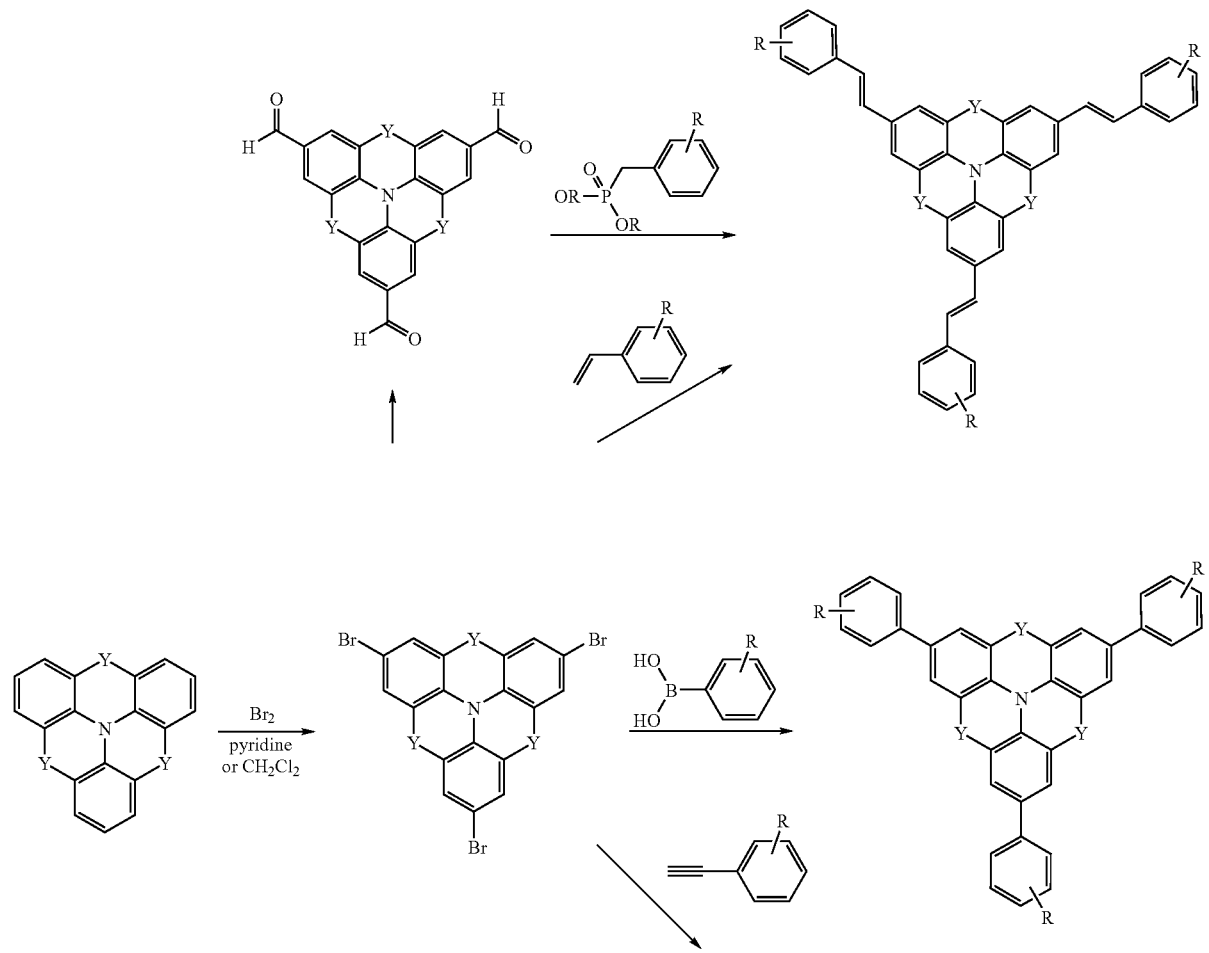

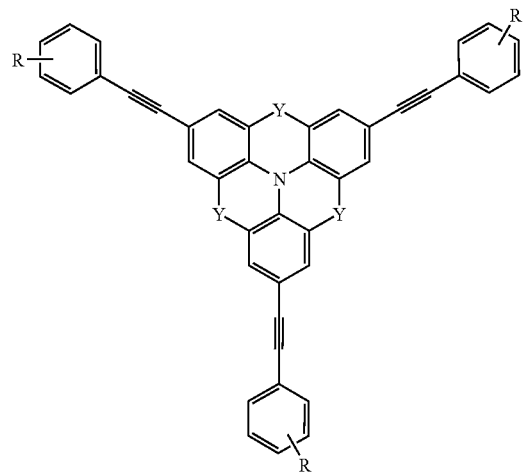

The invention therefore furthermore relates to a process for the preparation of compounds of the formula (1), characterised in that the unfunctionalised parent structure of the formula (1) in which all radicals R stand for hydrogen is functionalised, in particular brominated, and, in a further step, the substituents R are introduced.

Suitably functionalised compounds of the formula (1) or formula (2), in particular brominated compounds, such as, for example, structures (41) to (46) depicted above, can also be used for incorporation into polymers.

The invention therefore furthermore relates to polymers, oligomers or dendrimers containing recurring units of the formula (1) or formula (2). These polymers, oligomers or dendrimers may be conjugated, partially conjugated or non-conjugated. For the purposes of this application, an oligomer is intended to be taken to mean a compound containing at least three recurring units.

Further recurring units of the polymers, oligomers or dendrimers are preferably selected from the group consisting of fluorenes (for example in accordance with EP 842208 or WO 00/22026), spirobifluorenes (for example in accordance with EP 707020, EP 894107 or EP 04028865.6), paraphenylenes (for example in accordance with WO 92/18552), dihydrophenanthrenes (for example in accordance with WO 05/014689), phenanthrenes (for example in accordance with WO 05/104264 or the unpublished application DE 102005037334.3), indenofluorenes (for example in accordance with WO 04/041901 or WO 04/113412), carbazoles (for example in accordance with WO 04/070772), anthracenes, naphthalenes or thiophenes (for example in accordance with EP 1028136). Further preferred recurring units are fluorescent or phosphorescent emitting units, for example based on vinylarylamines or metal complexes, or hole-conducting units, in particular based on triarylamines. Polymers containing a plurality of these units or homopolymers of the recurring units of the formula (1) are also possible.

The compounds of the formula (1) and formula (2) can be employed in organic electronic devices, in particular in organic electroluminescent devices. For the purposes of this invention, an organic electronic device is taken to mean a device which has an anode, cathode and at least one layer which comprises at least one organic compound. In organic electroluminescent devices, at least one layer is an emitting layer. Apart from the cathode, anode and the emitting layer, the organic electroluminescent device may also comprise further layers. These can be, for example: hole-injection layer, hole-transport layer, electron-transport layer and/or electron-injection layer. However, it should be pointed out at this point that each of these layers does not necessarily have to be present.

Depending on the substitution, the compound of the formula (1) or formula (2) is employed in different functions or in different organic layers.

In a preferred embodiment of the invention, the compound in the emitting layer is employed as a mixture with at least one host material. This is the case, in particular, if at least one substituent R, preferably at least two substituents P, particularly preferably all three substituents R, of the compound of the formula (1) or formula (2) represents a $CR^2{=}CR^2Ar$ group. Furthermore, compounds of the formula (2) in which the symbol L stands for a —$CR^2{=}CR^2$— group are particularly suitable here.

A host material in a system comprising host and dopant is taken to mean the component which is present in the higher proportion in the system. In a system comprising one host and a plurality of dopants, the host is taken to mean the component whose proportion in the mixture is the highest.

The proportion of the host material in the emitting layer is between 50.0 and 99.9% by weight, preferably between 80.0 and 99.5% by weight, particularly preferably between 90.0 and 99.0% by weight. Correspondingly, the proportion of the dopant of the formula (1) or formula (2) is between 0.1 and 50.0% by weight, preferably between 0.5 and 20.0% by weight, particularly preferably between 1.0 and 10.0% by weight.

Suitable host materials are various classes of substance. Preferred host materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082) or the atropisomers (for example in accordance with the unpublished application EP 04026402.0). Particularly preferred host materials are selected from the classes of the oligoarylenes containing naphthalene, anthracene and/or pyrene or atropisomers of these compounds, the oligoarylenevinylenes, the ketones, the phosphine oxides and the sulfoxides. Very particularly preferred host materials are selected from the classes of the oligoarylenes containing anthracene and/or pyrene or atropisomers of these compounds, the phosphine oxides and the sulfoxides. For the purposes of this application, an oligoarylene is intended to be taken to mean a compound in which at least three aryl or arylene groups are bonded to one another.

Preference is furthermore given to organic electroluminescent devices, characterised in that a plurality of emitting compounds are used in the same layer or in different layers, where at least one of these compounds has a structure of the formula (1) or formula (2). These compounds particularly preferably have in total a plurality of emission maxima between 380 nm and 750 nm, overall resulting in white emission, i.e. apart from the compound of the formula (1) or formula (2), at least one further emitting compound which is able to fluoresce or phosphoresce and emits yellow, orange or red light is also used. Particular preference is given to three-layer systems, of which at least one of these layers comprises a compound of the formula (1) or formula (2) and where the layers exhibit blue, green and orange or red emission (for the basic structure see, for example, WO 05/011013).

In a further preferred embodiment of the invention, the compound of the formula (1) or formula (2) is employed as host material in an emitting layer. This is the case, in particular, if the substituents R stand for aromatic or heteroaromatic ring systems.

In still a further preferred embodiment of the invention, the compound of the formula (1) or formula (2) is employed as hole-transport material or hole-injection material in an organic electroluminescent device or another organic electronic device. The compounds are then preferably substituted by aromatic substituents R or groups of the formula $N(Ar)_2$. The compound is preferably employed in a hole-transport or hole-injection layer. For the purposes of this invention, a hole-injection layer is a layer which is directly adjacent to the anode. For the purposes of this invention, a hole-transport layer is a layer which is located between a hole-injection layer and an emission layer. If the compounds of the formula (1) or formula (2) are used as hole-transport or hole-injection material, it may be preferred for them to be doped with electron-acceptor compounds, for example with $F_4$-TCNQ or with compounds as described in EP 1476881 or EP 1596445. Compounds of the formula (1) and formula (2) have very high hole mobilities, which are possibly produced by stacking effects of the compounds. This class of compounds can thus also be employed for the production of anisotropic transport properties.

Preference is furthermore given to an organic electroluminescent device, characterised in that one or more layers are coated by means of a sublimation process, The materials are vapour-deposited here in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are coated by means of the OVPD (organic vapour phase deposition) process or with the aid of carrier-gas sublimation. The materials are applied here at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds.

The compounds according to the invention have the following surprising advantages over the prior art on use in organic electroluminescent devices:.

1. The efficiency of corresponding devices becomes higher compared with systems in accordance with the prior art, in particular compared with systems which do not contain any bridge elements.
2. The stability of corresponding devices becomes higher compared with systems in accordance with the prior art, which is evident, in particular, from a significantly longer lifetime.
3. The compounds can be sublimed and vapour-deposited well and without considerable decomposition, are consequently easier to process and are therefore more suitable for use in OLEDs than materials in accordance with the prior art.
4. The Stokes shift (difference between absorption and emission) is smaller than in the case of related compounds in an unbridged structure.
5. The compounds have high charge-carrier mobility.

The present application text and also the examples below are directed to the use of the compounds according to the invention in relation to OLEDs and PLEDs and the corresponding displays. In spite of this restriction of the description, it is possible for the person skilled in the art without further inventive step also to use the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photo receptors or organic laser diodes (O-lasers). The present invention likewise relates to the use of the compounds according to the invention in the corresponding devices and to these devices themselves.

The invention is explained in greater detail by the following examples without wishing to restrict it thereby.

EXAMPLES

The following syntheses are carried out under a protective-gas atmosphere, unless indicated otherwise. The starting materials can be purchased from ALDRICH or ABCR (methyl anthranilate, methyl 2-iodo-benzoate, palladium(II) acetate, tri-o-tolylphosphine, inorganics, solvents). The synthesis of 4,4,8,8,12,12-hexamethyl-2,6,10-tribromo-4H,8H,12H-benzo[1,9]quinolizino[3,4,5,6,7-defg]acridine is described in the literature (D. Hellwinkel, M. Melan, *Chem. Ber.* 1974, 107, 616-626).

Example 1

Synthesis of 4,4,8,8,12,12-hexamethyl-2,6,10-tribromo-4H,8H,12H-benzo[1,9]quinolizino[3,4,5,6,7-defg]acridine

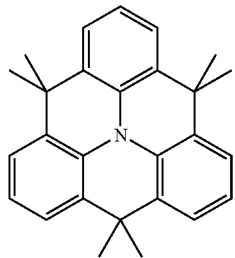

→

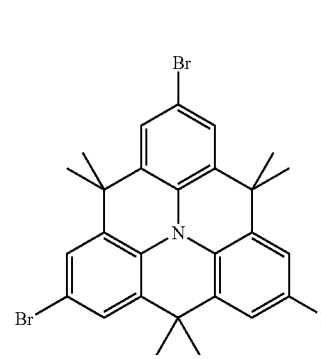

5.3 g (14.5 mmol) of 4,4,8,8,12,12-hexamethyl-4H,8H,12H-benzo[1,9]quinolizino-[3,4,5,6,7-defg]acridine are initially introduced in 150 ml of $CH_2Cl_2$. A solution of 8.0 g (45.1 mmol) of NBS in 100 ml of $CH_2Cl_2$ is subsequently added dropwise at 0° C. with exclusion of light, and the mixture is allowed to come to RT and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction.

Yield: 3 g (5 mmol), 57% of theory, purity according to $^1$H-NMR about 98%. This compound is employed as intermediate for the subsequent syntheses.

Example 2

Synthesis of 4,4,8,8,12,12-hexamethyl-2,6,10-triphenyl-4H,8H,12H-benzo[1,9]quinolizino[3,4,5,6,7-defg]acridine (HTM1)

HTM1

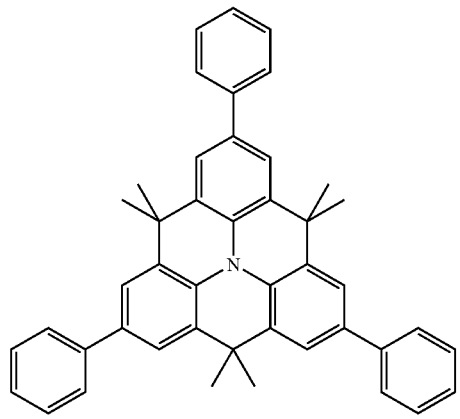

0.27 g (0.9 mmol) of tri-o-tolylphosphine and then 33.5 mg (0.15 mmol) of palladium(II) acetate are added with vigorous stirring to a degassed suspension of 3 g (5 mmol) of 2,6,10-tribromo-4,4,8,8,12,12-hexamethyl-4H,8H,12H-benzo[1,9]quinolizino[3,4,5,6,7-defg]acridine (from Example 1), 2.74 g (22.5 mmol) of phenylboronic acid and 7.8 g (31.5 mmol) of potassium phosphate hydrate in a mixture of 7.5 ml of dioxane, 15 ml of toluene and 18 ml of water. The mixture is boiled under reflux for 5 h and allowed to cool. The precipitate is filtered off with suction, washed three times with 10 ml of ethanol/water (1:1, v:v) and three times with 5 ml of ethanol and subsequently dried in vacuo. Yield: 2.4 g (4 mmol), 81% of theory, purity according to $^1$H-NMR about 98%.

Example 3

Synthesis of the Dopant D1

D1

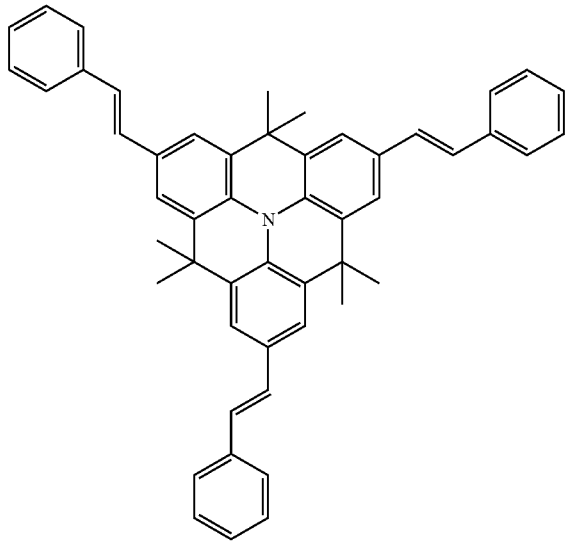

A mixture of 30.1 g (50 mmol) of 4,4,8,8,12,12-hexamethyl-2,6,10-tribromo-4H,8H,12H-benzo[1,9]quinolizino[3,4,5,6,7-defg]acridine (from Example 1), 25.8 ml (225 mmol) of styrene, 337 mg (1.5 mmol) of palladium(II) acetate, 1.55 g (15 mmol) of N,N-dimethylglycine, 81 mg (0.5 mmol) of iron(III) chloride and 37.8 g (450 mmol) of sodium hydrogencarbonate in 500 ml of NMP is slowly heated to 140° C. with vigorous stirring and subsequently stirred at this temperature for 16 h. After cooling, 500 ml of dichloromethane and 1000 ml of water are added. The organic phase is separated off and washed five times with 500 ml of water each time. After drying over sodium sulfate, the organic phase is evaporated to dryness. The resultant yellow solid is recrystallised six times from toluene, then washed twice by stirring with 500 ml of ethanol under reflux each time, giving 22 g (32 mmol) (corresponding to 68% of theory) of the product having a purity >99.4% according to HPLC.

Example 4

Synthesis of the Host Material H1

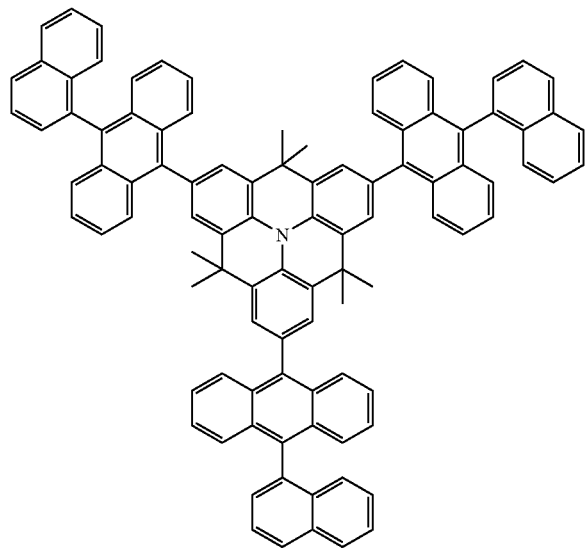

H1

1.3 g (1.17 mmol) of Pd(PPh$_3$)$_4$ are added to a nitrogen-saturated mixture of 6.2 g (10.4 mmol) of 4,4,8,8,12,12-hexamethyl-2,6,10-tribromo-4H,8H,12H-benzo[1,9]quinolizino[3,4,5,6,7-defg]acridine (from Example 1), 9.9 g (31.2 mmol) of 10-(1-naphthyl)-9-anthrylboronic acid, 14.9 g (70.2 mmol) of K$_3$PO$_4$, 200 ml of dioxane and 200 ml of water, and the suspension is heated at 80° C. for 7 h. 0.08 g of NaCN is then added, and the aqueous phase is separated off. The organic phase is washed twice with H$_2$O and dried over Na$_2$SO$_4$. The resultant residue is recrystallised from toluene. The deposited crystals are filtered off with suction, washed with 50 ml of ethanol and dried in vacuo, giving 10.4 g (8.1 mmol) (corresponding to 80% of theory) of the product having a purity >99.6% according to HPLC.

Example 5

DFT (Density Functional Theory) Calculations

Further information on the nature of planar triarylamines is given by the HOMO and LUMO energies and the band gaps. These quantities can be correlated with electron affinities, ionisation potentials, electronic transitions and reactivities. In order to calculate the energies of these molecules in the electronic ground state, DFT (density functional theory) calculations were carried out (Table 1). The structures here correspond to the structures description in the depiction. The excitation energies were estimated via the HOMO/LUMO gap. The b3pw91 base set was used for the calculations. In addition, the calculations have been calibrated via cyclic voltammetry data.

Example 6

Production of OLEDs

OLEDs are produced by a general process as described in WO 04/058911, which is adapted in individual cases to the respective circumstances (for example layer-thickness variation in order to achieve optimum efficiency or colour).

The results for various OLEDs are presented in the following examples. The basic structure, the materials and layer thicknesses used, apart from the emitting layer and the hole-injection and hole-transport layer, are identical for better comparability. OLEDs having the following structure are produced analogously to the general process mentioned above:

| | |
|---|---|
| Hole-injection layer (HIL) | 0 nm or 20 nm HTM1, see Table 1 |
| Hole-transport layer (HTL) | 40 nm or 20 nm NPB (vapour-deposited; N-naphthyl-N-phenyl-4,4'-diaminobiphenyl), see Table 1 |
| Emission layer (EML) | see Table 1 for materials, concentration 5%, layer thickness 30 nm |
| Electron conductor (ETL) | 20 nm Alq$_3$ (purchased from SynTec; tris(quinolinato)aluminium(III)) |
| LiF—Al (cathode) | 1 nm LiF, 150 nm Al on top. |

These OLEDs are characterised by standard methods; for this purpose, the electroluminescence spectra, the efficiency (measured in cd/A), the power efficiency (measured in lm/W) as a function of the luminance, calculated from current/voltage/luminous density characteristic lines (IUL characteristic lines), and the lifetime were determined. The lifetime is defined as the time after which the initial luminance of 1000 cd/m$^2$ has dropped to half.

Table 2 shows results for some OLEDs (Examples 7 to 9), where in each case the composition of the EML, HIL and HTL including the layer thicknesses is also shown. Example 7 shows the dopant D2 according to the prior art in the host material H1 according to the invention (from Example 4). Example 8 shows the host H2 in accordance with the prior art with the emission material D1 according to the invention (from Example 3). The OLED in Example 9 additionally comprises HTM1 (from Example 2) as hole-injection material. The structural formulae of dopant D2 used and of host material H2 in accordance with the prior art are depicted below:

TABLE 1

Results of the DFT calculations

| Example | HOMO (Hartrees) | HOMO [eV] | HOMO Corrected | LUMO (HARTREES) | LUMO [eV] | LUMO Corrected | GAP [eV] | λmax-theo [nm] |
|---|---|---|---|---|---|---|---|---|
| Structure (3) | −0.17519 | −4.77 | −5.14 | −0.03394 | −0.92 | −2.11 | 3.02 | 411 |
| Structure (19) | −0.17134 | −4.66 | −5.04 | −0.05484 | −1.49 | −2.52 | 2.52 | 493 |
| Structure (23) | −0.16639 | −4.53 | −4.92 | −0.03124 | −0.85 | −2.06 | 2.86 | 434 |

H2

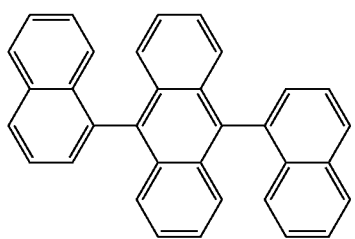

D2

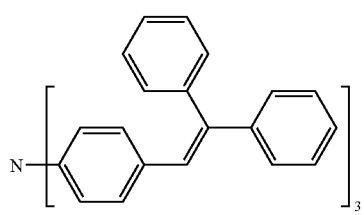

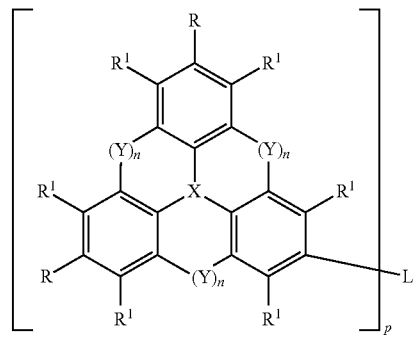

formula(2)

wherein
X is, identically or differently on each occurrence, N, P, As, Sb, P=, As=O, or Sb=O;
Y is, identically or differently on each occurrence, O, S, $C(R^1)_2$, C=O, C=S, C=NR$^1$, C=C(R$^1$)$_2$, Si(R$^1$)$_2$, BR$^1$, NR$^1$, PR$^1$, AsR$^1$, SbR$^1$, BiR$^1$, P(=O)R$^1$, As(=O)R$^1$, Sb(=O)R$^1$, Bi(=O)R$^1$, SO, SeO, TeO, SO$_2$, SeO$_2$, TeO$_2$, or a chemical bond;

TABLE 2

| Example | HIL | HTL | EML | Max. efficiency (cd/A) | Voltage (V) at 1000 cd/m² | CIE[a] | Lifetime (h)[b] |
|---|---|---|---|---|---|---|---|
| 7 |  | NPB (40 nm) | H1:D2 (5%) (30 nm) | 8.0 | 6.0 | x = 0.16 y = 0.24 | 3500 |
| 8 |  | NPB (40 nm) | H2:D1 (5%) (30 nm) | 4.1 | 6.5 | x = 0.15 y = 0.11 | 1500 |
| 9 | HTM1 (20 nm) | NPB (20 nm) | H2:D1 (5%) (30 nm) | 4.1 | 6.5 | x = 0.15 y = 0.13 | 1700 |

[a]CIE coordinates: colour coordinates of the Commission Internationale de l'Eclairage 1931.
[b]Lifetime: time until the luminance drops to 50% of the initial luminance, measured at an initial luminance of 1000 cd/m².

In summary, it can be stated that the compounds according to the invention, for example compounds HTM1, D1 and H1, are very highly suitable for use in organic electroluminescent devices and that organic electroluminescent devices which comprise these materials have very good properties.

The invention claimed is:
1. An organic electroluminescent device comprising at least one compound of formula (1) and/or a compound of formula (2)

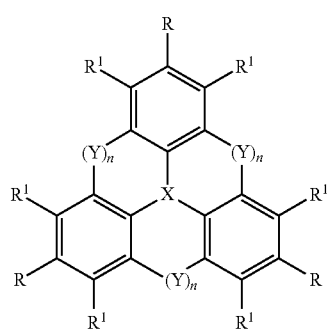

formula(1)

R$^1$ is, identically or differently on each occurrence, H, OH, F, Cl, Br, I, CN, CHO, NO$_2$, N(Ar)$_2$, Si(R$^2$)$_3$, B(OR$^2$)$_2$, C(=O)Ar, P(=O)Ar$_2$, S(=O)Ar, S(=O)Ar$_2$, CR$^2$=CR$^2$Ar, C≡CAr, OSO$_2$R$^2$, a straight-chain alkyl, alkoxy or thioalkoxy group having up to 40 C atoms optionally substituted by one or more radicals R$^2$, a branched or cyclic alkyl, alkoxy or thioalkoxy group having 3 to 40 C atoms optionally substituted by one or more radicals R$^2$, wherein one or more non-adjacent CH$_2$ groups are optionally replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, P(=O)R$^2$, S=O, SO$_2$, NR$^2$, —O—, —S—, or —CONR$^2$— and wherein one or more H atoms are optionally replaced by F, Cl, Br, I, CN or NO$_2$, an aromatic or heteroaromatic ring system having 5 to 40 aromatic ring atoms optionally substituted by one or more radicals R$^2$, or an aryloxy or heteroaryloxy group having 5 to 24 aromatic ring atoms optionally substituted by one or more radicals R$^2$, or a combination of two, three, four or five of these systems; and wherein two or more substituents R$^1$, either on the same ring or on different rings, optionally define a mono- or polycyclic, aliphatic, aromatic or heteroaromatic ring system with one another;
R is, identically or differently on each occurrence, in the compound of formula (2), H, OH, F, Cl, Br, I, CN, CHO, NO$_2$, N(Ar)$_2$, Si(R$^2$)$_3$, B(OR$^2$)$_2$, C(=O)Ar, P(=O)Ar$_2$, S(=O)Ar, S(=O)Ar$_2$, CR$^2$=CR$^2$Ar, C≡CAr, OSO$_2$R$^2$, a straight-chain alkyl group having up to 40 C atoms optionally substituted by one or more radicals R$^2$, a branched or cyclic alkyl group having 3 to 40 C atoms optionally substituted by one or more radicals R$^2$, wherein one or more non-adjacent CH$_2$ groups are optionally replaced by —R$^2$C═CR$^2$—, C≡C—, Si(R$^2$)$_2$, Ge(R$^2$)$_2$, Sn(R$^2$)$_2$, C═O, C═S, C═Se, C═NR$^2$, P(═O)R$^2$, S═O, SO$_2$, NR$^2$, —O—, —S—, or —CONR$^2$— and wherein one or more H atoms are optionally replaced by F, Cl, Br, I, CN or NO$_2$, an aromatic or heteroaromatic ring system having 5 to 40 aromatic ring atoms optionally substituted by one or more radicals R$^2$, or a combination of two, three, four or five of these systems; and wherein two or more substituents R$^1$, either on the same ring or on different rings, optionally define a mono- or polycyclic, aliphatic, aromatic or heteroaromatic ring system with one another; with the proviso that at least one radical R is not equal to hydrogen;
and
is, identically or differently on each occurrence in the compound of formula (1), H, CR$^2$═CR$^2$Ar, C≡CAr, or an aromatic or heteroaromatic ring system having 5 to 40 aromatic ring atoms optionally substituted by one or more radicals R$^2$, with the proviso that at least one radical R is not equal to hydrogen;

R$^2$ is, identically or differently on each occurrence, H or an aliphatic, aromatic, and/or heteroaromatic hydrocarbon radical having up to 20 C atoms, wherein two or more radicals R$^2$ optionally define a ring system with one another;

Ar is, identically or differently on each occurrence, an aromatic or heteroaromatic ring system having 5-30 aromatic ring atoms optionally substituted by one or more non-aromatic radicals R$^1$;

L is an at least divalent straight-chain alkylene, alkylidene, alkyleneoxy, or thioalkyleneoxy group having up to 40 C atoms optionally substituted by one or more radicals R$^2$, or a branched or cyclic alkylene, alkylidene, alkyleneoxy or thioalkyleneoxy group having 3 to 40 C atoms optionally substituted by one or more radicals R$^2$, wherein one or more non-adjacent CH$_2$ groups are optionally replaced by —CR$^2$═CR$^2$—, C≡C, Si(R$^2$)$_2$, Ge(R$^2$)$_2$, Sn(R$^2$)$_2$, C═O, C═S, C═Se, C═NR$^2$, P(═O)R$^2$, S═O, SO$_2$, —O—, —S—, or —CONR$^2$— and wherein one or more H atoms are optionally replaced by F, Cl, Br, I, CN, or NO$_2$, an at least divalent aromatic or heteroaromatic ring system having 5 to 40 aromatic ring atoms optionally substituted by one or more radicals R$^2$, P(R$^1$)$_{3-p}$, P(═O)(R$^1$)$_{3-p}$, C(R$^1$)$_{4-p}$, Si(R$^1$)$_{4-p}$, N(Ar)$_{3-p}$, or a combination of two, three, four or five of these systems; or is a chemical bond;

n is, identically or differently on each occurrence, 0, 1, or 2, wherein when n =0, a hydrogen or R$^1$ is present instead of Y, with the proviso that at least two n are not equal to 0;

p is 2, 3, 4, 5, or 6, with the proviso that p is not greater than the maximum valency of L.

2. The organic electroluminescent device of claim 1, wherein X is nitrogen, phosphorus, or P═O.

3. The organic electroluminescent device of claim 1, wherein Y is, identically or differently on each occurrence, O, S, C(R$^1$)$_2$, C═O, P(═O)R$^1$, C═C(R$^1$)$_2$, NR$^1$, SO, SO$_2$, or a chemical bond.

4. The organic electroluminescent device of claim 1, wherein R$^1$ is, identically or differently on each occurrence, H, F, CF$_3$, OCH$_3$, OCF$_3$, an aliphatic, aromatic, or heteroaromatic hydrocarbon radical having up to 10 C atoms, or in that R$^1$ on bridges Y stands for an aliphatic hydrocarbon radical having up to 6 C atoms or for an aryl or heteroaryl group having 6 to 10 C atoms, wherein two radicals R$^1$ on the same bridge Y optionally define a ring system with one another.

5. The organic electroluminescent device of claim 1, wherein R is, identically or differently on each occurrence, CR$^2$═CR$^2$Ar, C≡CAr, or an aromatic or heteroaromatic ring system having 5 to 30 aromatic ring atoms, optionally substituted by one or more non-aromatic radicals R$^2$.

6. The organic electroluminescent device of claim 1, wherein L is —CR$^2$═CR$^2$—, —C≡C—, C═O, S═O, SO$_2$, —O—, —S—, P(R$^1$)$_{3-p}$, P(═O)(R$^1$)$_{3-p}$, C(R$^1$)$_{4-p}$, Si(R$^1$)$_{4-p}$, N(Ar)$_{3-p}$, or an aromatic or heteroaromatic ring system having 6 to 30 aromatic ring atoms, optionally substituted by one or more radicals R$^2$, or a combination of two, three or four of these systems or a chemical bond.

7. An organic electroluminescent device comprising at least one compound of formula (1) and/or a compound of formula (2)

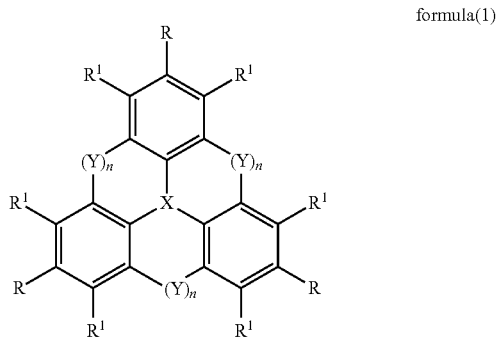

formula(1)

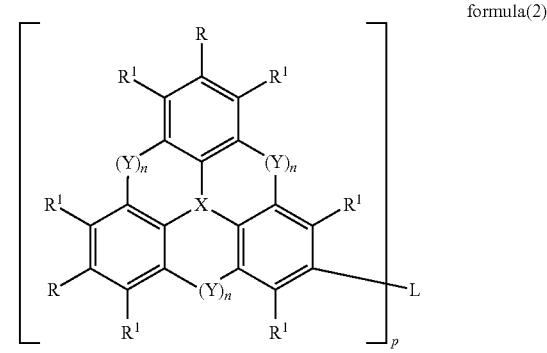

formula(2)

wherein
X is, identically or differently on each occurrence, N, P, As, Sb, P═O, As═O, or Sb═O;
Y is, identically or differently on each occurrence, O, S, C(R$^1$)$_2$, C═O, C═S, C═NR$^1$, C═C(R$^1$)$_2$, Si(R$^1$)$_2$, BR$^1$, NR$^1$, PR$^1$, AsR$^1$, SbR$^1$, BiR$^1$, P(═O)R$^1$, As(═O)R$^1$, Sb(═O)R$^1$, Bi(═O)R$^1$, SO, SeO, TeO, SO$_2$, SeO$_2$, TeO$_2$, or a chemical bond;
R$^1$ is, identically or differently on each occurrence, H, OH, F, Cl, Br, I, CN, CHO, NO$_2$, N(Ar)$_2$, Si(R$^2$)$_3$, B(OR$^2$)$_2$, C(═O)Ar, P(═O)Ar$_2$, S(═O)Ar, S(═O)Ar$_2$, CR$^2$═CR$^2$Ar, C≡CAr, OSO$_2$R$^2$, a straight-chain alkyl, alkoxy or thioalkoxy group having up to 40 C atoms optionally substituted by one or more radicals R$^2$, a branched or cyclic alkyl, alkoxy or thioalkoxy group having 3 to 40 C atoms optionally substituted by one or more radicals R$^2$, wherein one or more non-adjacent CH$_2$ groups are optionally replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, P(=O)R$^2$, S=O, SO$_2$, NR$^2$, —O—, —S—, or —CONR$^2$— and wherein one or more H atoms are optionally replaced by F, Cl, Br, I, CN or NO$_2$, an aromatic or heteroaromatic ring system having 5 to 40 aromatic ring atoms optionally substituted by one or more radicals R$^2$, or an aryloxy or heteroaryloxy group having 5 to 24 aromatic ring atoms optionally substituted by one or more radicals R$^2$, or a combination of two, three, four or five of these systems; and wherein two or more substituents R', either on the same ring or on different rings, optionally define a mono- or polycyclic, aliphatic, aromatic or heteroaromatic ring system with one another, or is a bond;

R is, identically or differently on each occurrence, H, OH, F, Cl, Br, I, CN, CHO, NO$_2$, N(Ar)$_2$, Si(R$^2$)$_3$, B(OR$^2$)$_2$, C(=O)Ar, P(=O)Ar$_2$, S(=O)Ar, S(=O)Ar$_2$, CR$^2$=CR$^2$Ar, C≡CAr, OSO$_2$R$^2$, a straight-chain alkyl group having up to 40 C atoms optionally substituted by one or more radicals R$^2$, a branched or cyclic alkyl group having 3 to 40 C atoms optionally substituted by one or more radicals R$^2$, wherein one or more non-adjacent CH$_2$ groups are optionally replaced by —R$^2$C=CR$^2$—, —C≡C—, Si(R$^2$)$_2$, Ge(R$^2$)$_2$, Sn(R$^2$)$_2$, C=O, C=S, C=Se, C=NR$^2$, P(=O)R$^2$, S=O, SO$_2$, NR$^2$, —O—, —S—, or —CONR$^2$— and wherein one or more H atoms are optionally replaced by F, Cl, Br, I, CN or NO$_2$, an aromatic or heteroaromatic ring system having 5 to 40 aromatic ring atoms optionally substituted by one or more radicals R$^2$, or a combination of two, three, four or five of these systems; and wherein two or more substituents either on the same ring or on different rings, optionally define a mono- or polycyclic, aliphatic, aromatic or heteroaromatic ring system with one another; with the proviso that at least one radical R is not equal to hydrogen, or is a bond;

R$^2$ is, identically or differently on each occurrence, H or an aliphatic, aromatic, and/or heteroaromatic hydrocarbon radical having up to 20 C atoms, wherein two or more radicals R$^2$ optionally define a ring system with one another;

Ar is, identically or differently on each occurrence, an aromatic or heteroaromatic ring system having 5-30 aromatic ring atoms optionally substituted by one or more non-aromatic radicals R$^1$;

L is an at least divalent straight-chain alkylene, alkylidene, alkyleneoxy, or thioalkyleneoxy group having up to 40 C atoms optionally substituted by one or more radicals R$^2$, or a branched or cyclic alkylene, alkylidene, alkyleneoxy or thioalkyleneoxy group having 3 to 40 C atoms optionally substituted by one or more radicals R$^2$, wherein one or more non-adjacent CH$_2$ groups are optionally replaced by —CR$^2$=CR$^2$—, —C≡C—, Si(R$^2$)$_2$, Ge(R$^2$)$_2$, Sn(R$^2$)$_2$, C=O, C=S, C=Se, C=NR$^2$, P(=O)R$^2$, S=O, SO$_2$, —O—, —S—, or —CONR$^2$— and wherein one or more H atoms are optionally replaced by F, Cl, Br, I, CN, or NO$_2$, an at least divalent aromatic or heteroaromatic ring system having 5 to 40 aromatic ring atoms optionally substituted by one or more radicals R$^2$, P(R$^1$)$_{3-p}$, P(=O)(R$^1$)$_{3-p}$, C(R$^1$)$_{4-p}$, Si(R$^1$)$_{4-p}$, N(Ar)$_{3-p}$, or a combination of two, three, four or five of these systems; or is a chemical bond;

n is, identically or differently on each occurrence, 0, 1, or 2, wherein when n =0, a hydrogen or R$^1$ is present instead of Y, with the proviso that at least two n are not equal to 0;

p is 2, 3, 4, 5, or 6, with the proviso that p is not greater than the maximum valency of L; and with the proviso that said compound is not:

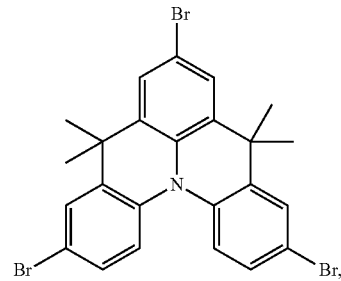 [SMILES: CC1(C)c2cc(Br)ccc2N2c3ccc(Br)cc3C(C)(C)c3cc(Br)cc1c32]

wherein said organic electroluminescent device comprises a polymer, oligomer, or dendrimer comprising at least one compound of formula (1) and/or compound of formula (2) as recurring units, wherein at least one R or R$^1$ of said at least one compound of formula (1) and/or compound of formula (2) is a bond to said polymer, oligomer, or dendrimer.

8. The organic electroluminescent device of claim 1, wherein said organic electroluminescent device comprises an anode, a cathode, and at least one emitting layer, wherein said at least one emitting layer comprises at least one compound of formula (1) and/or a compound of formula (2).

9. The organic electroluminescent device of claim 8, wherein said at least one compound of formula (1) and/or a compound of formula (2) is employed as a mixture with at least one host material and/or wherein said at least one compound formula (1) and/or compound of formula (2) is employed as hole-transport and/or hole-injection material.

10. A compound of formula (1) and/or a compound of formula (2)

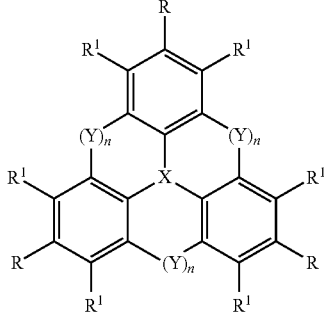

formula(1)

-continued

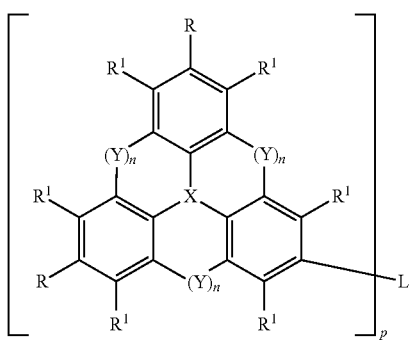

formula(2)

wherein
- X is, identically or differently on each occurrence, N, P, As, Sb, P=O, As=O, or Sb=O;
- Y is, identically or differently on each occurrence, O, S, $C(R^1)_2$, C=O, C=S, $C=NR^1$, $C=C(R^1)_2$, $Si(R^1)_2$, $BR^1$, $NR^1$, $PR^1$, $AsR^1$, $SbR^1$, $BiR^1$, $P(=O)R^1$, $As(=O)R^1$, $Sb(=O)R^1$, $Bi(=O)R^1$, SO, SeO, TeO, $SO_2$, $SeO_2$, $TeO_2$, or a chemical bond;
- $R^1$ is, identically or differently on each occurrence, H, OH, F, Cl, Br, I, CN, CHO, $NO_2$, $N(Ar)_2$, $Si(R^2)_3$, $B(OR^2)_2$, $C(=O)Ar$, $P(=O)Ar_2$, $S(=O)Ar$, $S(=O)Ar_2$, $CR^2=CR^2Ar$, C≡CAr, $OSO_2R^2$, a straight-chain alkyl, alkoxy or thioalkoxy group having up to 40 C atoms optionally substituted by one or more radicals $R^2$, a branched or cyclic alkyl, alkoxy or thioalkoxy group having 3 to 40 C atoms optionally substituted by one or more radicals $R^2$, wherein one or more non-adjacent $CH_2$ groups are optionally replaced by $-R^2C=CR^2-$, $-C≡C-$, $Si(R^2)_2$, $Ge(R^2)_2$, $Sn(R^2)_2$, C=O, C=S, C=Se, $C=NR^2$, $P(=O)R^2$, S=O, $SO_2$, $NR^2$, -O-, -S-, or $-CONR^2-$ and wherein one or more H atoms are optionally replaced by F, Cl, Br, I, CN or $NO_2$, an aromatic or heteroaromatic ring system having 5 to 40 aromatic ring atoms optionally substituted by one or more radicals $R^2$, or an aryloxy or heteroaryloxy group having 5 to 24 aromatic ring atoms optionally substituted by one or more radicals $R^2$, or a combination of two, three, four or five of these systems; and wherein two or more substituents $R^1$, either on the same ring or on different rings, optionally define a mono- or polycyclic, aliphatic, aromatic or heteroaromatic ring system with one another;
- R is, identically or differently on each occurrence in the compound of formula (1), H, $CR^2=CR^2Ar$, C≡CAr, or an aromatic or heteroaromatic ring system having 5 to 40 aromatic ring atoms optionally substituted by one or more radicals $R^2$; with the proviso that at least one radical R is not equal to hydrogen
  and
  is, identically or differently on each occurrence in the compound of formula (2), H, OH, F, Cl, Br, I, CN, CHO, $NO_2$, $N(Ar)_2$, $Si(R^2)_3$, $B(OR^2)_2$, $C(=O)Ar$, $P(=O)Ar_2$, $S(=O)Ar$, $S(=O)Ar_2$, $CR^2=CR^2Ar$, C≡CAr, $OSO_2R^2$, a straight-chain alkyl, alkoxy or thioalkoxy group having up to 40 C atoms optionally substituted by one or more radicals $R^2$, a branched or cyclic alkyl, alkoxy or thioalkoxy group having 3 to 40 C atoms optionally substituted by one or more radicals $R^2$, wherein one or more non-adjacent $CH_2$ groups are optionally replaced by $-R^2C=CR^2-$, C≡C, $Si(R^2)_2$, $Ge(R^2)_2$, $Sn(R^2)_2$, C=O, C=S, C=Se, $C=NR^2$, $P(=O)R^2$, S=O, $SO_2$, $NR^2$, -O-, -S-, or $-CONR^2-$ and wherein one or more H atoms are optionally replaced by F, Cl, Br, I, CN or $NO_2$, an aromatic or heteroaromatic ring system having 5 to 40 aromatic ring atoms optionally substituted by one or more radicals $R^2$, or an aryloxy or heteroaryloxy group having 5 to 24 aromatic ring atoms optionally substituted by one or more radicals $R^2$, or a combination of two, three, four or five of these systems; and wherein two or more substituents $R^1$, either on the same ring or on different rings, optionally define a mono- or polycyclic, aliphatic, aromatic or heteroaromatic ring system with one another; with the proviso that at least one radical R is not equal to hydrogen;
- $R^2$ is, identically or differently on each occurrence, H or an aliphatic, aromatic, and/or heteroaromatic hydrocarbon radical having up to 20 C atoms, wherein two or more radicals $R^2$ optionally define a ring system with one another;
- Ar is, identically or differently on each occurrence, an aromatic or heteroaromatic ring system having 5-30 aromatic ring atoms optionally substituted by one or more non-aromatic radicals $R^I$;
- L is an at least divalent straight-chain alkylene, alkylidene, alkyleneoxy, or thioalkyleneoxy group having up to 40 C atoms optionally substituted by one or more radicals $R^2$, or a branched or cyclic alkylene, alkylidene, alkyleneoxy or thioalkyleneoxy group having 3 to 40 C atoms optionally substituted by one or more radicals $R^2$, wherein one or more non-adjacent $CH_2$ groups are optionally replaced by $-CR^2=CR^2-$, $-C≡C-$, $Si(R^2)_2$, $Ge(R^2)_2$, $Sn(R^2)_2$, C=O, C=S, C=Se, $C=NR^2$, $P(=O)R^2$, S=O, $SO_2$, -O-, -S-, or $-CONR^2-$ and wherein one or more H atoms are optionally replaced by F, Cl, Br, I, CN, or $NO_2$, an at least divalent aromatic or heteroaromatic ring system having 5 to 40 aromatic ring atoms optionally substituted by one or more radicals $R^2$, $P(R^1)_{3-p}$, $P(=O)(R^1)_{3-p}$, $C(R^1)_{4-p}$, $Si(R^1)_{4-p}$, $N(Ar)_{3-p}$, or a combination of two, three, four or five of these systems; or is a chemical bond;
- n is, identically or differently on each occurrence, 0, 1, or 2, wherein when n =0, a hydrogen or $R^1$ is present instead of Y, with the proviso that at least two n are not equal to 0;
- p is 2, 3, 4, 5, or 6, with the proviso that p is not greater than the maximum valency of L.

11. The compound of claim 10, wherein X is nitrogen, phosphorus, or P=O.

12. The compound of claim 10, wherein Y is, identically or differently on each occurrence, O, S, $C(R^1)_2$, C=O, $P(=O)R^1$, $C=C(R^1)_2$, $NR^1$, SO, $SO_2$, or a chemical bond.

13. The compound of claim 10, wherein $R^I$ is, identically or differently on each occurrence, H, $CF_3$, $OCH_3$, $OCF_3$, an aliphatic, aromatic, or heteroaromatic hydrocarbon radical having up to 10 C atoms, or in that $R^1$ on bridges Y stands for an aliphatic hydrocarbon radical having up to 6 C atoms or for an aryl or heteroaryl group having 6 to 10 C atoms, wherein two radicals $R^1$ on the same bridge Y optionally define a ring system with one another.

14. The compound of claim 10, wherein R is, identically or differently on each occurrence, $CR^2=CR^2Ar$, C≡CAr, or an aromatic or heteroaromatic ring system having 5 to 30 aromatic ring atoms, optionally substituted by one or more non-aromatic radicals $R^2$.

15. The compound of claim 10, wherein L is —CR²═CR²—, —C≡C—, C═O, S═O, SO₂, —O—, —S—, P(R¹)₃₋ₚ, P(═O)(R¹)₃₋ₚ, C(R¹)₄₋ₚ, Si(R¹)₄₋ₚ, N(Ar)₃₋ₚ, or an aromatic or heteroaromatic ring system having 6 to 30 aromatic ring atoms, optionally substituted by one or more radicals R², or a combination of two, three or four of these systems or a chemical bond.

16. A polymer, oligomer, or dendrimer comprising one or more compounds of formula (1) and/or formula (2)

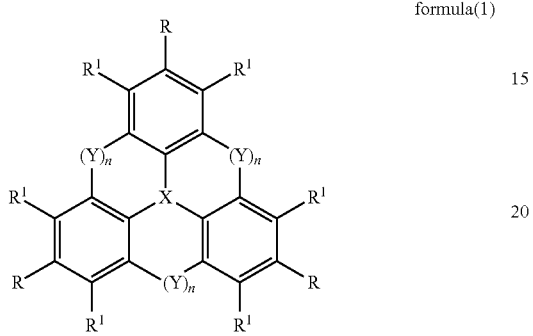

formula(1)

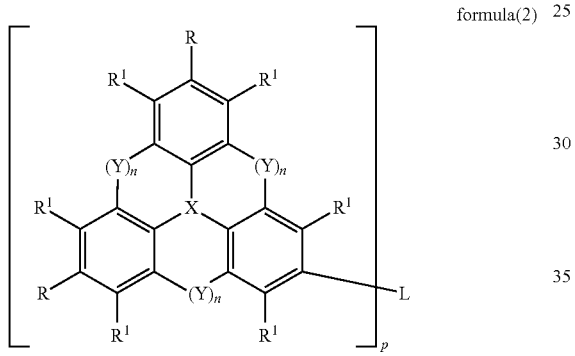

formula(2)

wherein

X is, identically or differently on each occurrence, N, P, As, Sb, P═O, As═O, or Sb═O;

Y is, identically or differently on each occurrence, O, S, C(R¹)₂, C═O, C═S, C═NR¹, C═C(R¹)₂, Si(R¹)₂, BR¹, NR¹, PR¹, AsR¹, SbR¹, BiR¹, P(═O)R¹, As(═O) R¹, Sb(═O)R¹, Bi(═O)R¹, SO, SeO, TeO, SO₂, SeO₂, TeO₂, or a chemical bond;

R¹ is, identically or differently on each occurrence, H, OH, F, Cl, Br, I, CN, CHO, NO₂, N(Ar)₂, Si(R²)₃, B(OR²)₂, C(═O)Ar, P(═O)Ar₂, S(═O)Ar, S(═O)Ar₂, CR²═CR²Ar, C≡CAr, OSO₂R², a straight-chain alkyl, alkoxy or thioalkoxy group having up to 40 C atoms optionally substituted by one or more radicals R², a branched or cyclic alkyl, alkoxy or thioalkoxy group having 3 to 40 C atoms optionally substituted by one or more radicals R², wherein one or more non-adjacent CH₂ groups are optionally replaced by —R²C═CR²—, C≡C—, Si(R²)₂, Ge(R²)₂, Sn(R²)₂, C═O, C═S, C═Se, C═NR², P(═O)R², S═O, SO₂, NR², —O—, —S—, or —CONR²— and wherein one or more H atoms are optionally replaced by F, Cl, Br, I, CN or NO₂, an aromatic or heteroaromatic ring system having 5 to 40 aromatic ring atoms optionally substituted by one or more radicals R², or an aryloxy or heteroaryloxy group having 5 to 24 aromatic ring atoms optionally substituted by one or more radicals R², or a combination of two, three, four or five of these systems; and wherein two or more substituents R¹, either on the same ring or on different rings, optionally define a mono- or polycyclic, aliphatic, aromatic or heteroaromatic ring system with one another, or is a bond;

R is, identically or differently on each occurrence in the compound of formula (1), H, CHO, B(OR²)₂, P(R²)₂, CR²═CR²Ar, C≡CAr, or an aromatic or heteroaromatic ring system having 5 to 30 aromatic ring atoms, optionally substituted by one or more non-aromatic radicals R¹, or a combination of two, three, four or five of these radicals, or is a bond, and is, identically or differently on each occurrence in the compound of formula (2), H, OH, F, Cl, Br, I, CN, CHO, NO₂, N(Ar)₂, Si(R²)₃, B(OR²)₂, C(═O)Ar, P(═O)Ar₂, S(═O)Ar, S(═O)Ar₂, CR²═CR²Ar, C≡CAr, OSO₂R², a straight-chain alkyl, alkoxy or thioalkoxy group having up to 40 C atoms optionally substituted by one or more radicals R², a branched or cyclic alkyl, alkoxy or thioalkoxy group having 3 to 40 C atoms optionally substituted by one or more radicals R², wherein one or more non-adjacent CH₂ groups are optionally replaced by —R²C═CR²—, C≡C-, Si(R²)₂, Ge(R²)₂, Sn(R²)₂, C═O, C═S, C═Se, C═NR², P(═O)R², S═O, SO₂, NR², —O—, —S—, or —CONR²— and wherein one or more H atoms are optionally replaced by F, Cl, Br, I, CN or NO₂, an aromatic or heteroaromatic ring system having 5 to 40 aromatic ring atoms optionally substituted by one or more radicals R², or an aryloxy or heteroaryloxy group having 5 to 24 aromatic ring atoms optionally substituted by one or more radicals R², or a combination of two, three, four or five of these systems; and wherein two or more substituents R', either on the same ring or on different rings, optionally define a mono- or polycyclic, aliphatic, aromatic or heteroaromatic ring system with one another; with the proviso that at least one radical R is not equal to hydrogen, or is a bond;

R² is, identically or differently on each occurrence, H or an aliphatic, aromatic, and/or heteroaromatic hydrocarbon radical having up to 20 C atoms, wherein two or more radicals R² optionally define a ring system with one another;

Ar is, identically or differently on each occurrence, an aromatic or heteroaromatic ring system having 5-30 aromatic ring atoms optionally substituted by one or more non-aromatic radicals R¹;

L is an at least divalent straight-chain alkylene, alkylidene, alkyleneoxy, or thioalkyleneoxy group having up to 40 C atoms optionally substituted by one or more radicals R², or a branched or cyclic alkylene, alkylidene, alkyleneoxy or thioalkyleneoxy group having 3 to 40 C atoms optionally substituted by one or more radicals R², wherein one or more non-adjacent CH₂ groups are optionally replaced by —CR²═CR²—, —C≡C-, Si(R²)₂, Ge(R²)₂, Sn(R²)₂, C═O, C═S, C═Se, C═NR², P(═O)R², S═0, SO₂, —O—, —S—, or —CONR²— and wherein one or more H atoms are optionally replaced by F, Cl, Br, I, CN, or NO₂, an at least divalent aromatic or heteroaromatic ring system having 5 to 40 aromatic ring atoms optionally substituted by one or more radicals R², P(R¹)₃₋ₚ, P(═O) (R¹)₃₋ₚ, C(R¹)₄₋ₚ, Si(R¹)₄₋ₚ, N(Ar)₃₋ₚ, or a combination of two, three, four or five of these systems; or is a chemical bond;

n is, identically or differently on each occurrence, 0, 1, or 2, wherein when n =0, a hydrogen or $R^1$ is present instead of Y, with the proviso that at least two n are not equal to 0;

p is 2, 3, 4, 5, or 6, with the proviso that p is not greater than the maximum valency of L, as recurring units, wherein at least one R or $R^1$ of said one or more compounds of formula (1) and/or formula (2) is a bond to said polymer, oligomer, or dendrimer.

17. A process for preparing compounds of claim 10, comprising functionalizing the unfuntionalized parent structure of formula (1) wherein all the radicals R are hydrogen is functionalized and introducing substituents R onto the functionalized parent structure of formula (1).

18. The process of claim 17, wherein said functionalizing is achieved by brominating said unfuntionalized parent structure of formula (1).

19. The organic electroluminescent device of claim 8, wherein said at least one compound of formula (1) and/or compound of formula (2) is present in said at least one emitting layer as a dopant material in combination with a host material.

20. The organic electroluminescent device of claim 19, wherein said host material is selected from the group consisting of oligoarylenes containing naphthalene, anthracene, pyrene, mixtures thereof, and atropisomers thereof, oligoarylenevinylenes, ketones, phosphine oxides, and sulfoxides.

21. The organic electroluminescent device of claim 8, wherein said at least one compound of formula (1) and/or compound of formula (2) is present in said at least one emitting layer as a host material in combination with a dopant material.

22. The organic electroluminescent device of claim 21, wherein said at least one compound of formula (1) and/or compound of formula (2) is present in said emitting layer in a concentration of 80 to 99.5% by weight.

* * * * *